United States Patent [19]

Shen

[11] Patent Number: 5,906,207
[45] Date of Patent: May 25, 1999

[54] METHOD FOR SIMULATING HEART FAILURE

[75] Inventor: You-Tang Shen, Lansdale, Pa.

[73] Assignee: Merck & Co., Inc., Rahway, N.J.

[21] Appl. No.: 08/826,316

[22] Filed: Mar. 27, 1997

Related U.S. Application Data

[60] Provisional application No. 60/014,864, Apr. 4, 1996, and provisional application No. 60/038,307, Feb. 27, 1997.

[51] Int. Cl.$^6$ .................................................. A61B 19/00
[52] U.S. Cl. .......................... 128/898; 514/421; 514/486
[58] Field of Search ................................... 128/898, 920; 514/421, 486; 600/509

[56] References Cited

U.S. PATENT DOCUMENTS

| | | |
|---|---|---|
| 4,664,125 | 5/1987 | Pinto . |
| 4,930,517 | 6/1990 | Cohen et al. . |
| 5,153,178 | 10/1992 | Maroko . |
| 5,215,083 | 6/1993 | Drane et al. . |

OTHER PUBLICATIONS

Calderone et al. "Dysfunction of the Beta–ADN Alph–Adrenergic Systems in a Model of Congestive Heart Failure" Circ Res (USA) 69(2):332–343, 1991.

Shannon et al. "Impaired Regional Subendocardial Coronary Flow Reserve in Conscious Dogs with Pacing–Induced Heart Failure" Am J Physiol Heart Circ Physiol (USA) 265(3):34–3 (h801–h809), 1993.

Masaki et al. "Production of Chronic Congestive Heart Failure by Rapid Ventricular Pacing in Teh Rabbit" Cardiovasc Res 27(5):828–831, 1993.

Iannini et al. "The Identification of Contributory Mechanisms for the Development and Progression of Congestive Heart Failure in Animal Models" J Heart Lung Transplant 15(11):1138–1150, 1996.

C. Mavroudis, et al., "Creation of Left–to–Right Shunts in the Newborn Pig: A New Model", J. of Surgical Research, vol. 36, pp. 274–277. (1984).

L. J. van Woerkens, et al., "Cardiovascular Effects of Dopamine and Dobutamine in Conscious Pigs with Chronic Heart Failure", vol. 21(3) pp. 420–424, (1993).

W. J. van der Giessen, et al., "Nisoldipine Improves Blood Flow to Skeletal Muscles in Conscious Pigs with Chronic Heart Failure", vol. 11, pp. 552–559, (1990).

J. Zhang, et al., "Functional and Bioenergetic Consequences of Postinfarction Left Ventricular Remodeling in a New Porcine Model", Circulation, vol. 94(5) pp. 1089–1100, (1996).

G. P. Eising, et al., "Force–Frequency Relations During Heart Failure in Pigs", American Physiological Society, vol. 267 pp. H2516–H2522, (1994).

D. J. Farrar, et al., "Isolated Systoclic and Diastolic Ventricular Interactions in Pacing–Induced Dilated Cardiomyopathy and Effects of Volume Loading and Pericardium", Circulation, vol. 92(5), pp. 1284–1290, (1995).

J. L. Zellner, et al., "Alterations in Myocyte Shape and Basement Membrane Attachment With Tachycardia–Induced Heat Failure", Circulation Research, vol. 69, pp. 590–600, (1991).

I. J. LeGrice, et al., Impaired Subendocardial Function in Tachycardia–Induced Cardiac Failure, American Physiological Society, vol. 268, pp. H1788–H1794, (1995).

E. Chow, et al., "Rapid Ventricular Pacing in Pigs: An Experimental Model of Congestive Heart Failure", American Physiological Society, vol. 258, pp. H1603–H1605, (1990).

*Primary Examiner*—Mickey Yu
*Assistant Examiner*—Kelly O'Hara
*Attorney, Agent, or Firm*—Valerie J. Camara; Mark R. Daniel

[57] ABSTRACT

A method of chronically instrumenting an animal enabling one to simulate congestive heart failure. A method for assessing the effects of a test compound on cardiac function and systemic vascular dynamics.

14 Claims, 33 Drawing Sheets

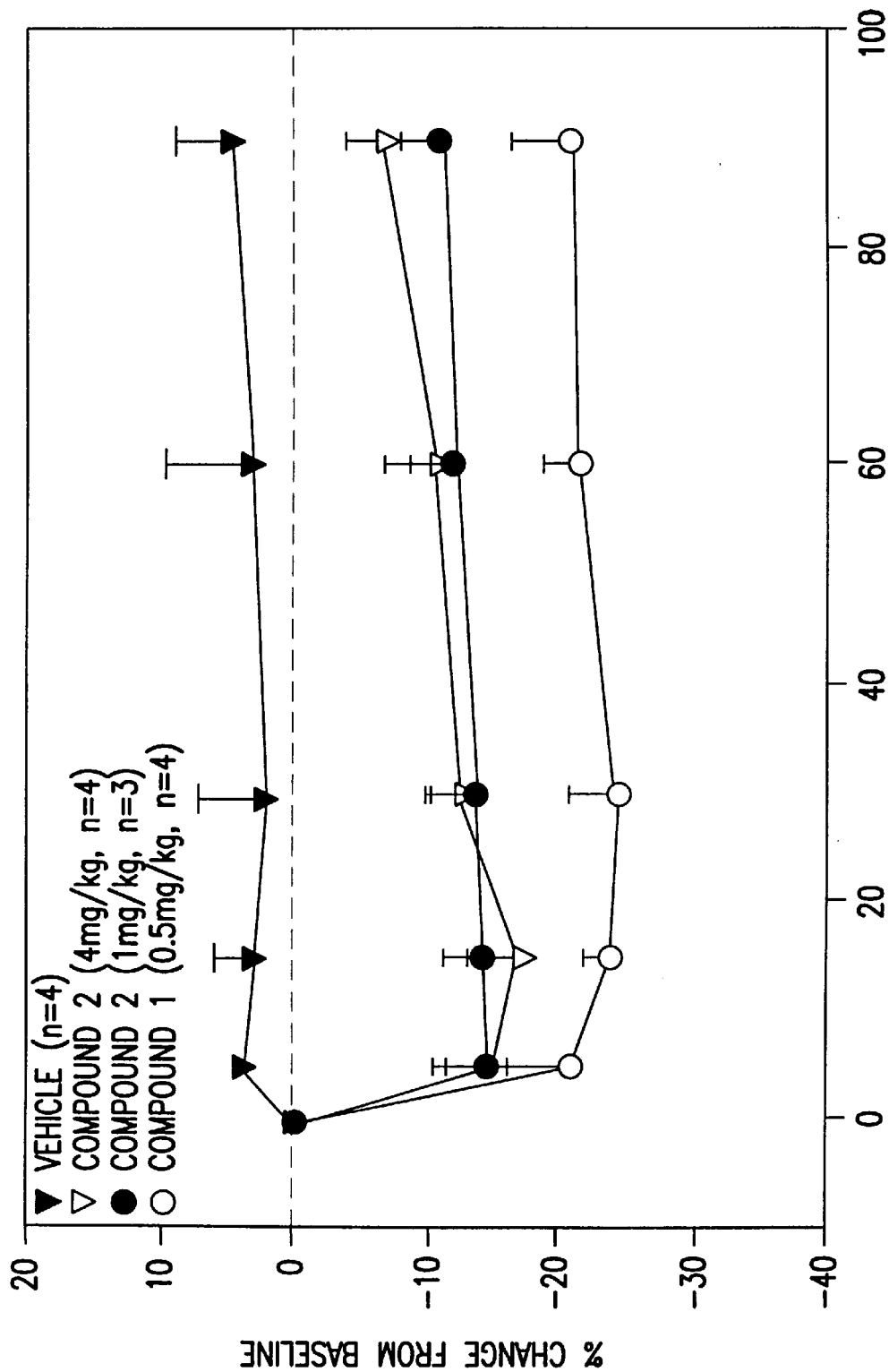

METHOD FOR SIMULATING HEART FAILURE

RELATED APPLICATIONS

The present application is a non-provisional application claiming priority from U.S. provisional application Ser. No. 60/014,864 (Case 19670PV) filed Apr. 4, 1996, now abandoned; GB application No. 9617950.2 filed Aug. 28, 1996; and U.S. provisional application Ser. No. 60/038,307 (Case 19670PV2) filed Feb. 27, 1997 now abandoned.

BACKGROUND OF THE INVENTION

The preclinical assessment of agents for the treatment of heart failure has been hampered by the lack of appropriate animal models. Previous models have either utilized non-clinically relevant insults to induce the disease state, or have failed to produce controllable, stable and predictable damage. Pressure overloading to induce ventricular hypertrophy and failure, produced by a variety of techniques including corticosteroid administration, renal artery occlusion, unilateral nephrectomy with contralateral occlusion of the renal artery, and most extensively banding of major outflow tracts such as the aorta, has been used in a variety of species including rat, cat and dog (Smith and Nutall, *Cardiovascular Research* 19: 181–186, 1985).

However, acute severe fixed afterload augmentation in animal models probably differs significantly from the gradual events that occur with pressure overload failure in man. The major limitation of animal pressure overload models include the propensity for the development of hypertrophy but not failure and/or a protracted time frame for the development of failure. Volume overloading produced by arteriovenous fistulae and valvular incompetence has been used to induce heart failure in dogs; however, this method has been limited by difficulty in controlling the degree of cardiac damage (Smith and Nutall, *Cardiovascular Research* 19: 181–186, 1985).

Cardiotoxic agents, including doxorubicin, have been used in several species including rat and dog to induce heart failure. This approach is limited by difficulty in controlling dose of cardiotoxic agent to induce sufficient but not excessive damage, extracardiac toxicity and the production of calcium overload-injury that may render the model unsuitable for the assessment of positive inotropic agents (Czarnecki, *Comparative Biochemistry and Physiology* 79C: 9–14, 1984; Smith and Nutall, *Cardiovascular Research* 19: 181–186, 1985). Several experimental procedures have been utilized to effect coronary artery occlusion, myocardial ischemia and resultant heart failure primarily in rats and dogs. These procedures include direct coronary ligation, embolism with liquid mercury, injection of preformed thrombus, wedged catheters, and sequential coronary microembolization with microspheres (Khomaziuk et al, *Kardiologiya* 5: 19–23, 1965; Rees and Redding, *Cardiovascular Research* 2: 43–53, 1968; Lumicao et al, *American Journal of Medical Science* 261: 27–40, 1971; Millner et al, *Annals of Thoracic Surgery* 52: 78–83, 1991; Sabbah et al, *American Journal of Physiology* 260: H1379–H1384, 1991). Problems associated with coronary artery ligation/ischemia models of heart failure include the inability of ischemic rodent models to develop myocardial dysfunction which meets the hemodynamic criteria of heart failure, as well as a high degree of malignant arrhythmia and mortality associated with myocardial ischemia. Damage to the heart from repeated DC shocks has been shown to induce heart failure in dogs (McDonald et al, *Journal of the American College of Cardiology* 19: 460–467, 1992); however the clinical relevance of this method of damage is uncertain.

Recently, several laboratories have adopted the method of rapid ventricular pacing-induced heart failure in dogs (Riegger and Liebau, *Clinical Science* 62: 465–469, 1982). One prominent criticism of the pacing-induced dog failure model is that while it does induce a predictable, controllable degree of myocardial failure, this condition is reversible with the termination of pacing. Also, the underlying mechanism for the development of failure in the pacing model is not understood at this time.

SUMMARY OF THE INVENTION

This invention relates to a method for determining whether a test compound is therapeutically useful for the treatment of heart failure, including but not limited to congestive heart failure. The assay employs a chronically instrumented conscious pig with heart failure wherein the heart failure is induced by myocardial ischemia and intermittent rapid cardiac pacing and provides a method for assessing the effects of the test compound on cardiac function and systemic vascular function.

BRIEF DESCRIPTION OF THE FIGURES

FIG. 5. Effects of Compound 1 (0.5 mg/kg, i.v.) and Compound 2 (1 mg/kg and 4 mg/kg, i.v.) on total peripheral resistance in conscious pigs after development of heart failure. Values are expressed as the percent changes from baseline levels. Data are mean±SE and the number of animals studied is in parenthesis.

DETAILED DESCRIPTION OF THE INVENTION

Figure 1A:
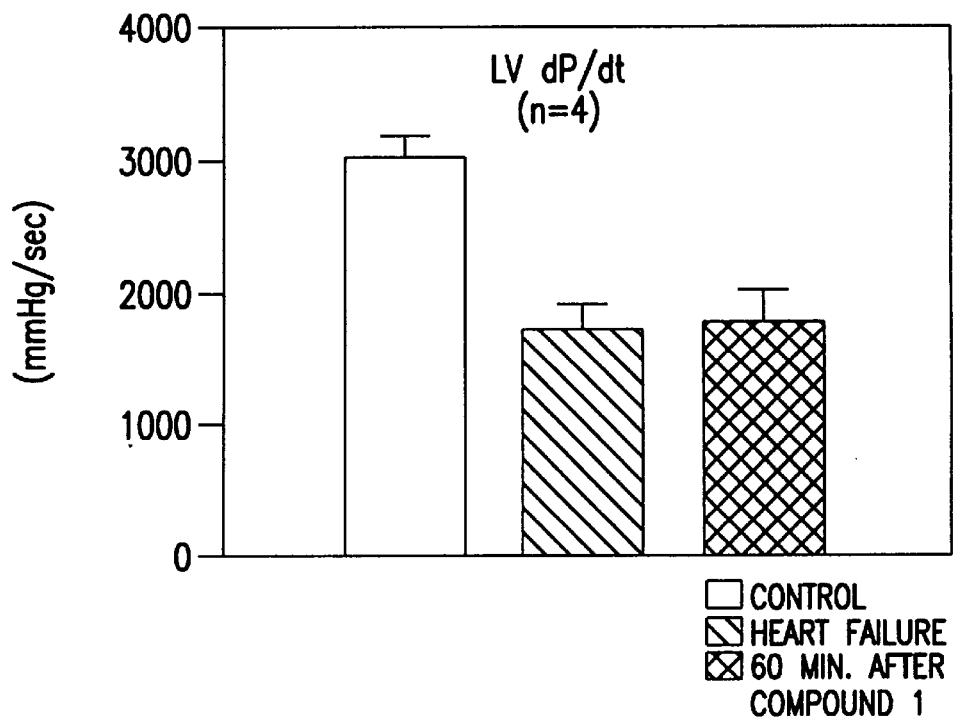
FIG. 1. Measurements of LV dP/dt, mean left atrial pressure, mean arterial pressure and heart rate made in the same conscious pigs before and after development of heart failure, and 60 min after injection of Compound 1 (0.5 mg/kg, i.v.) during the heart failure stage. Data are mean±SE and the number of animals studied is in parenthesis.
Figure 1B:
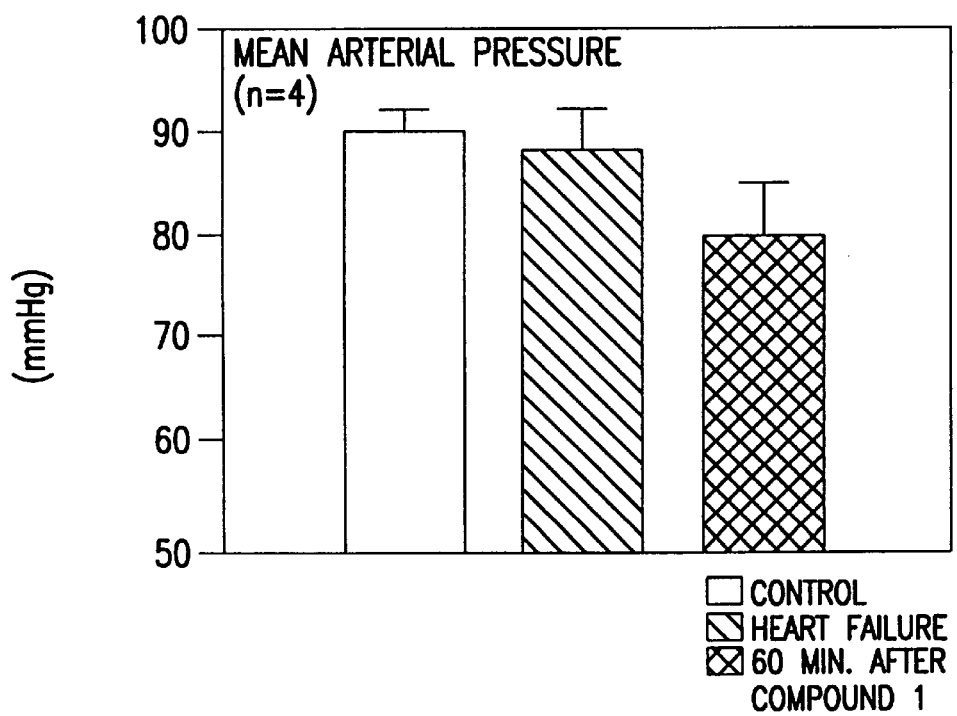
Figure 1C:
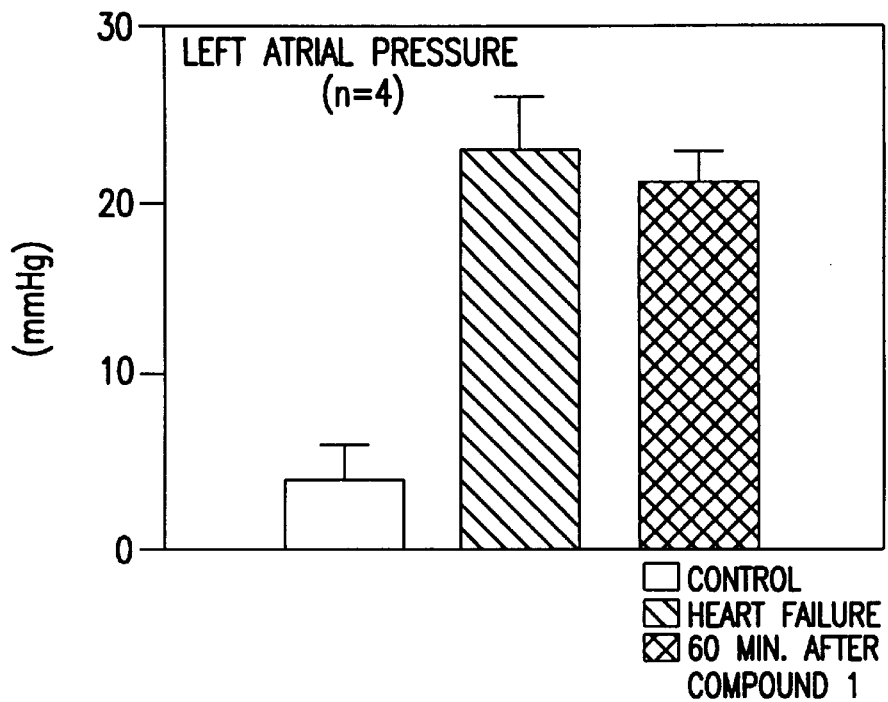
Figure 1D:
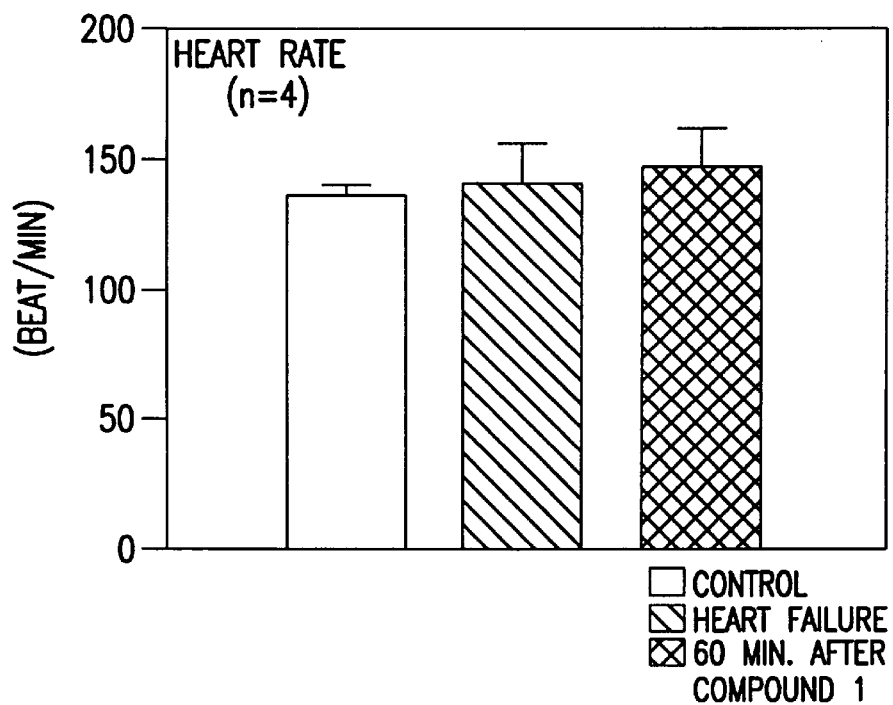
Figure 2A:
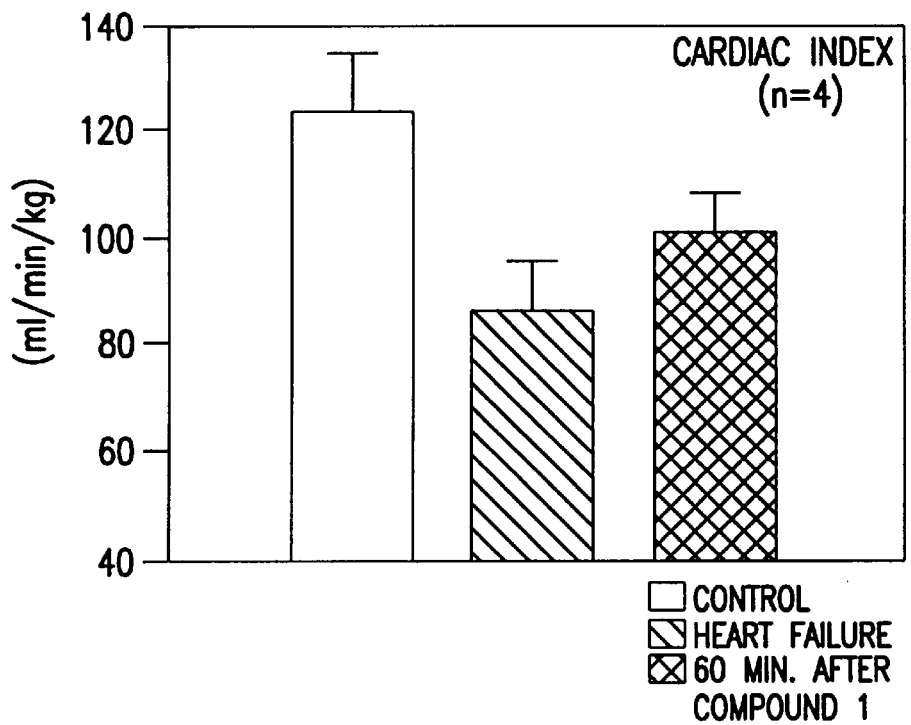
FIG. 2. Measurements of cardiac index, stroke volume, total peripheral resistance and LV velocity of circumferential fibre shortening (Vcf) made in the same conscious pigs before and after development of heart failure, and 60 min after injection of Compound 1 (0.5 mg/kg, i.v.) during the heart failure stage. Data are mean±SE and the number of animals studied is in parenthesis.
Figure 2B:
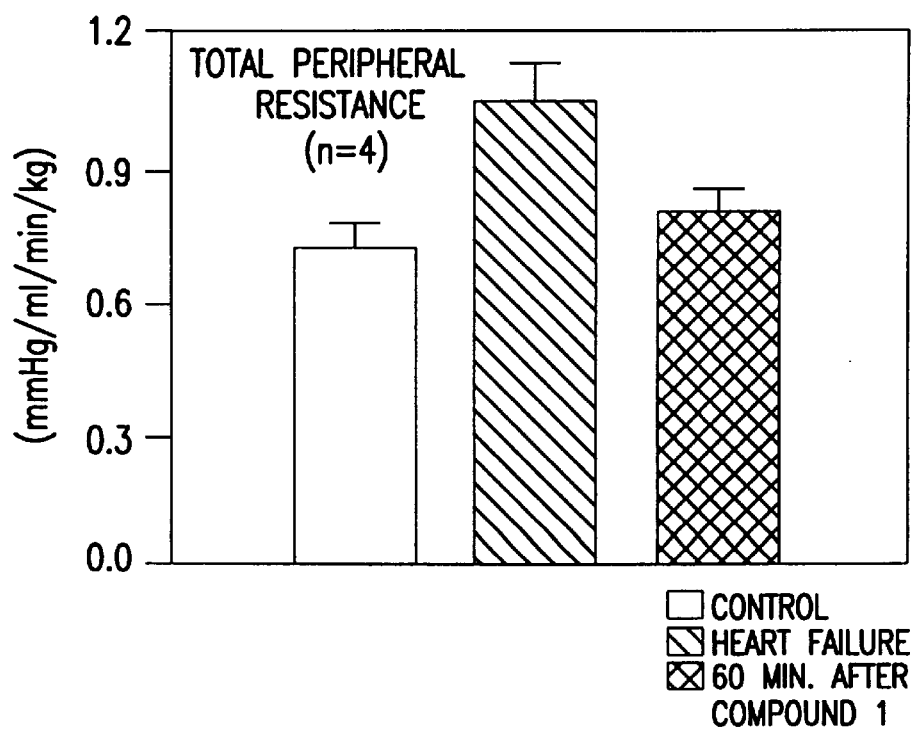
Figure 2C:
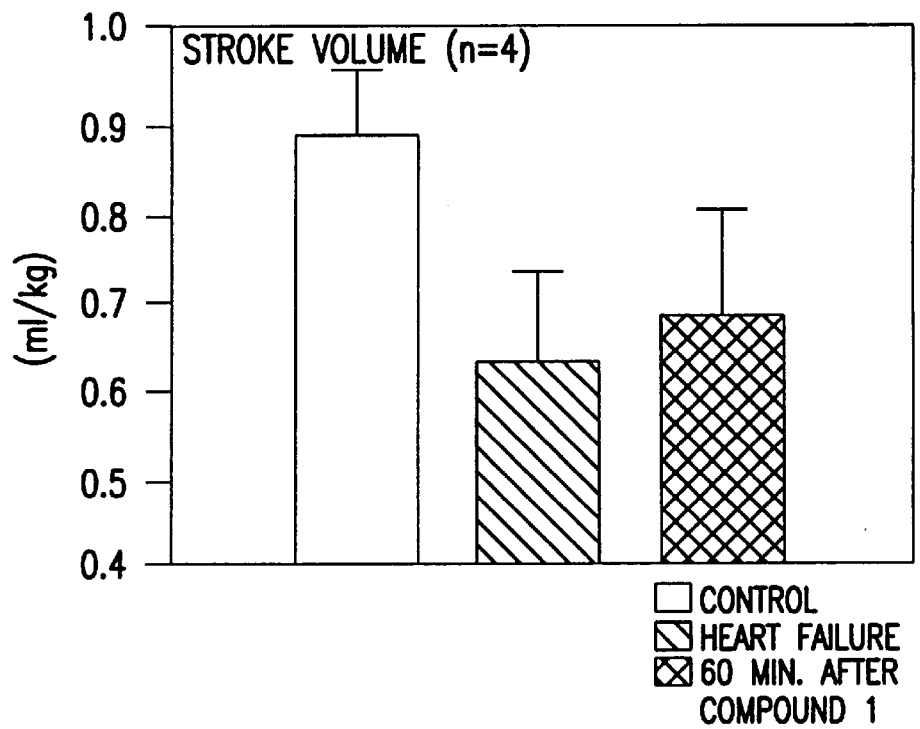
Figure 2D:
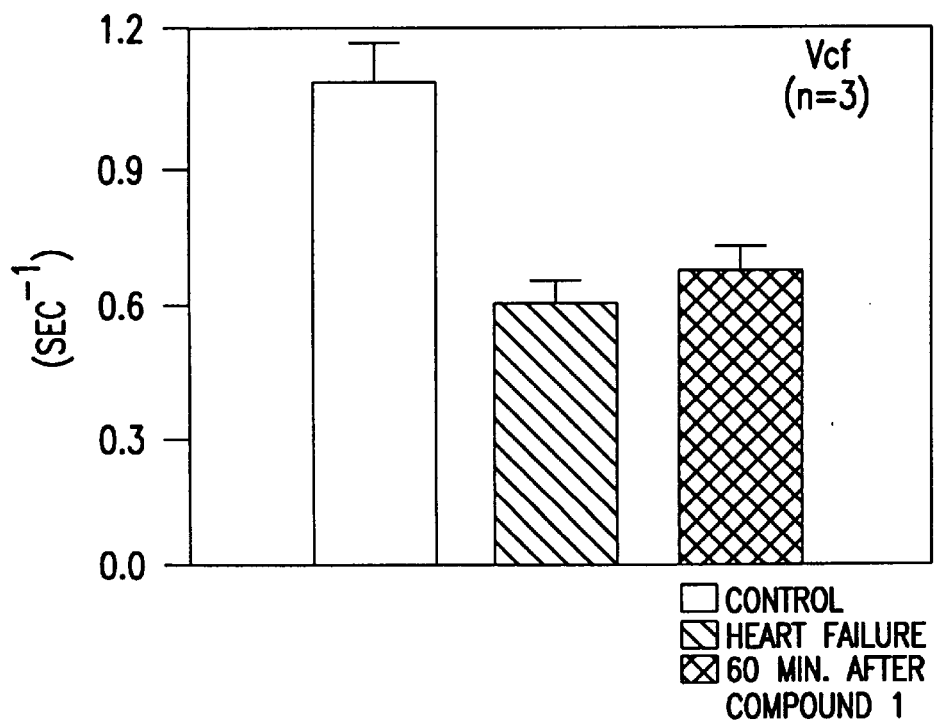
Figure 3A:
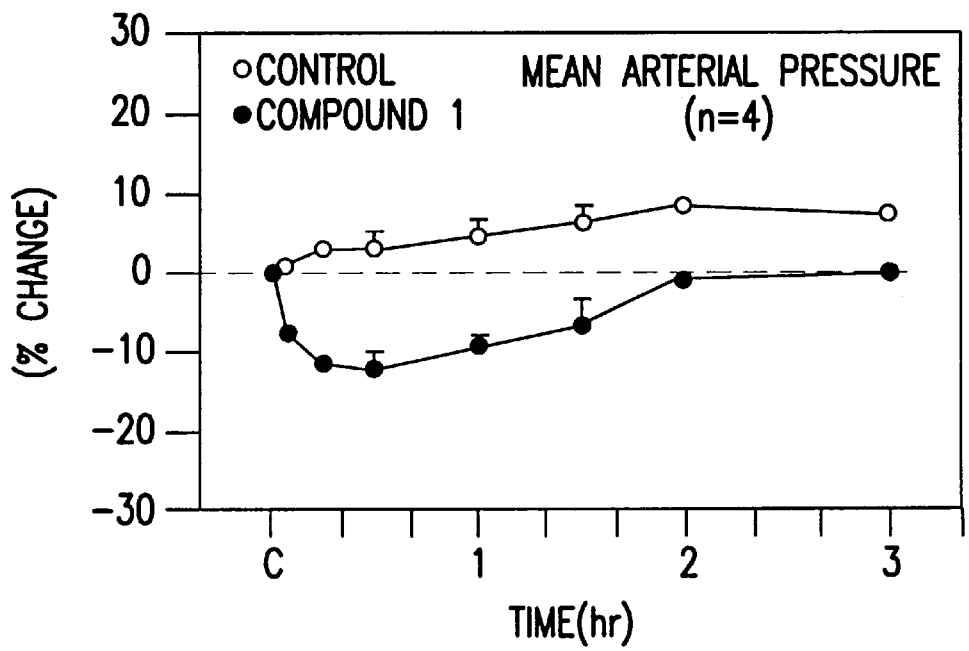
FIG. 3. Effects of Compound 1 (0.5 mg/kg, i.v.) on mean arterial pressure, mean left atrial pressure, cardiac index and total peripheral resistance in conscious pigs after development of heart failure. Values are expressed as the percent changes from baseline levels, except mean left atrial pressure which is change from baseline value in mmHg. Data are mean±SE and the number of animals studied is in parenthesis.
Figure 3B:
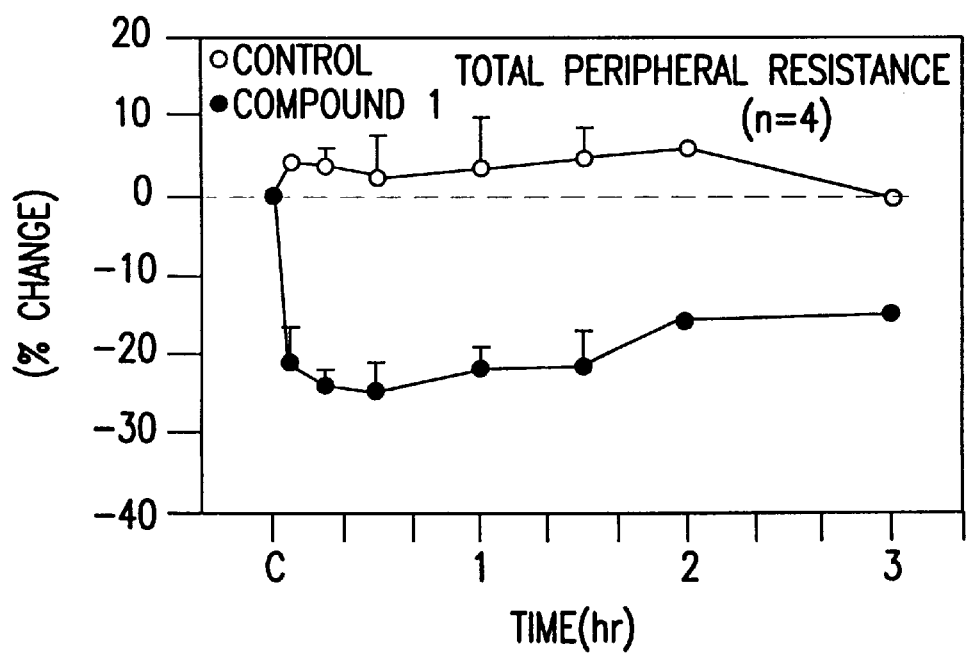
Figure 3C:
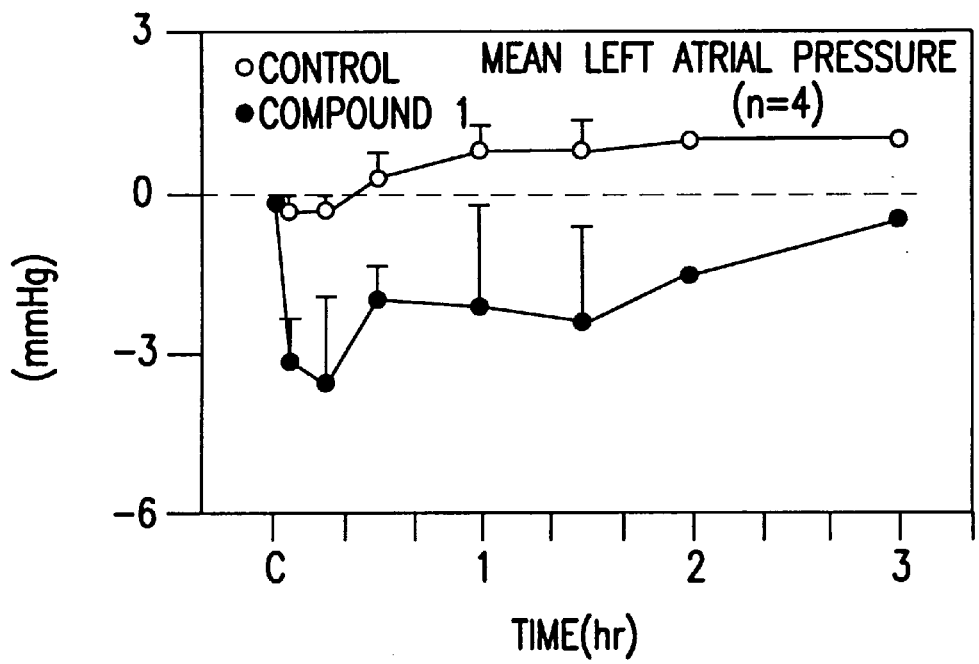
Figure 3D:
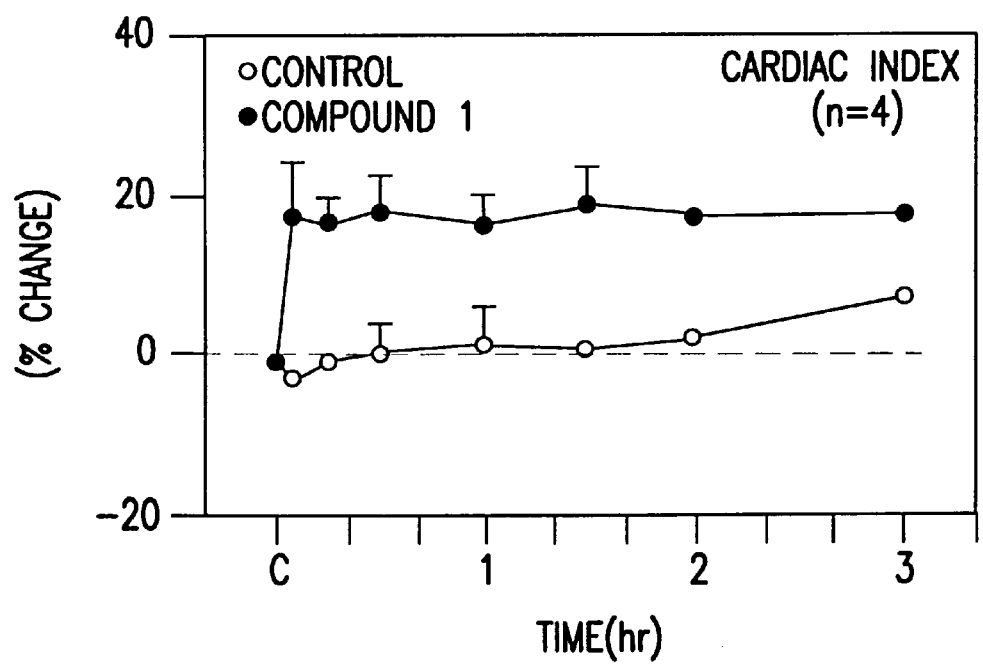
Figure 4A:
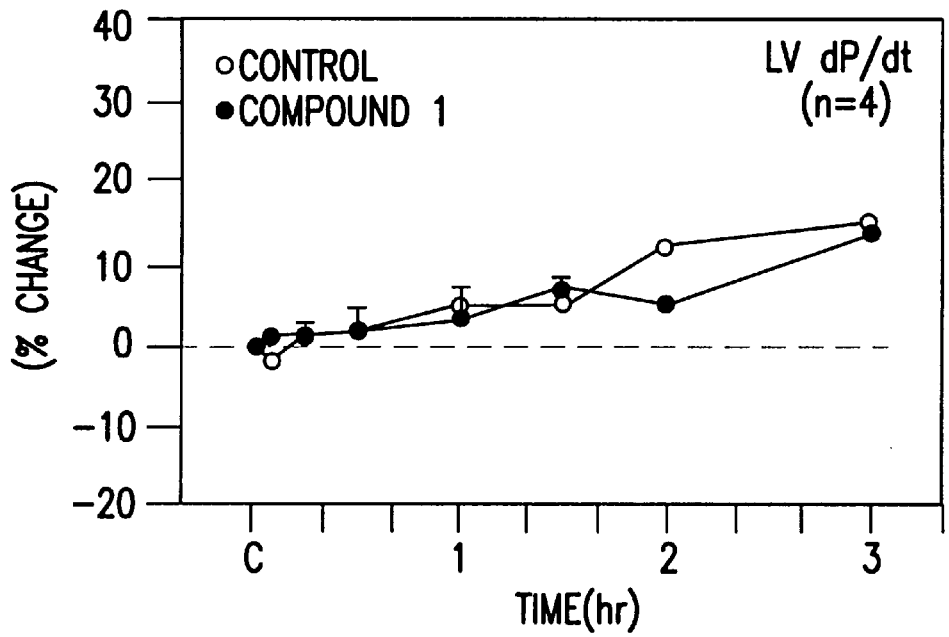
FIG. 4. Effects of Compound 1 (0.5 mg/kg, i.v.) on LV dP/dt, LV velocity of circumferential fibre shortening (Vcf), LV fractional shortening and heart rate in conscious pigs after development of heart failure. Values are expressed as the percent changes from baseline levels. Data are mean±SE and the number of animals studied is in parenthesis.
Figure 4B:
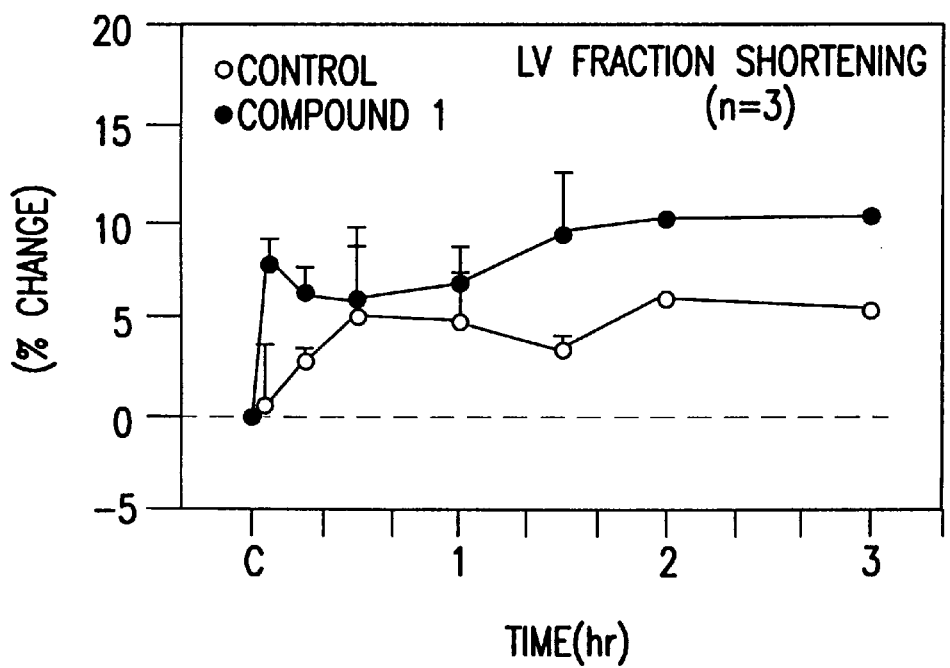
Figure 4C:
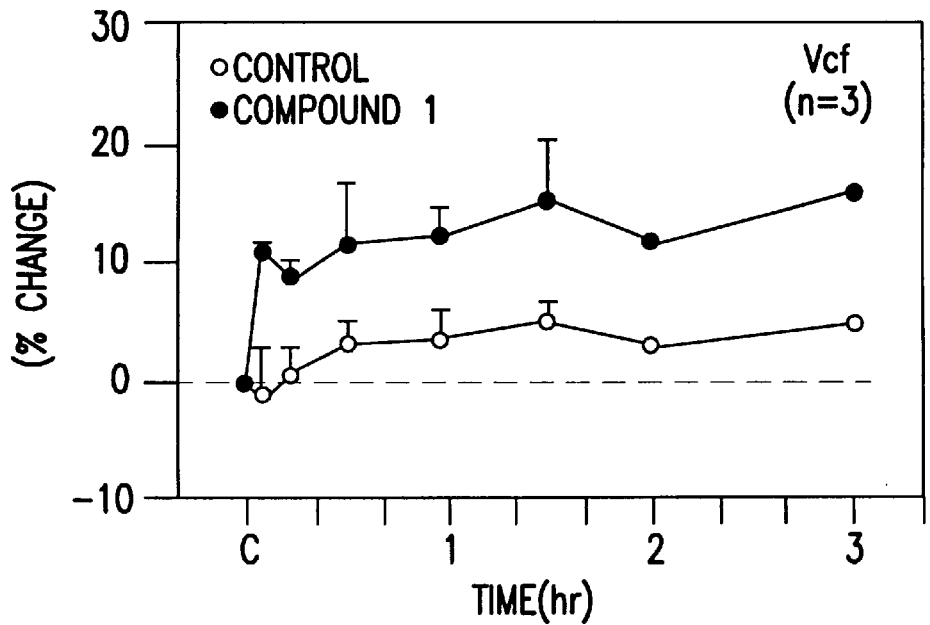
Figure 4D:
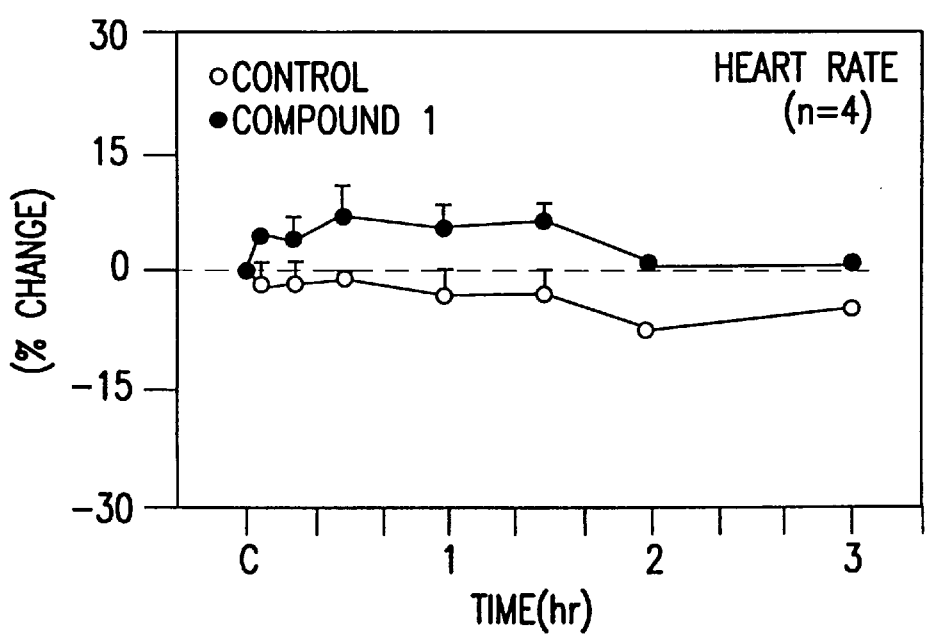

The invention relates to a method for simulating heart failure in a conscious, instrumented animal comprising the steps of:
(a) producing myocardial ischemia in the instrumented animal; and
(b) introducing rapid cardiac pacing in the instrumented animal, until the hemodynamic measurements, wherein hemodynamic measurements include: left atrial pressures; arterial pressure; aortic blood flow; total peripheral resistance; LV end-diastolic dimension; LV end systolic dimension; fractional shortening, mean velocity of circumferential fibre shortening and regional blood flows by radiolabeled microspheres; are indicative of heart failure.

An embodiment of this invention relates to the method for simulating heart failure in a conscious, instrumented animal as recited above, wherein production of myocardial ischemia comprises the steps of:
(a) inflating the distally implanted hydraulic occluder to occlude the distal left circumflex coronary artery about 7 to 10 days after the surgery to instrument the animal;
(b) waiting about 6 hours to 30 days after the distal left circumflex coronary artery occlusion; and
(c) inflating the proximally implanted hydraulic occluder to occlude the proximal left circumflex coronary artery.

A further embodiment of this invention relates to the method for simulating heart failure in a conscious, instrumented animal as recited above, wherein the rapid cardiac pacing comprises the steps of:
(a) using a cardiac pacemaker to introduce rapid cardiac pacing at a rate of about 190–210 beats/minute for about 1 to 7 days;
(b) waiting for about 0 to 72 hours after the first pacing; and
(c) repeating steps (a) and (b) at least until the hemodynamic measurements, wherein hemodynamic measurements include: left atrial pressures; arterial pressure; aortic blood flow; total peripheral resistance; LV end-diastolic dimension; LV end systolic dimension; fractional shortening, mean velocity of circumferential fibre shortening and regional blood flows by radiolabeled microspheres; are indicative of heart failure.

The invention relates to the method for simulating heart failure in a conscious, instrumented animal as recited above, wherein the rapid cardiac pacing is introduced in the left or right ventricle.

The invention relates to the method for simulating heart failure in a conscious, instrumented animal as recited above, wherein the rapid cardiac pacing is introduced in the left or right atrium.

The invention relates to the method for simulating heart failure in a conscious, instrumented animal as recited above, wherein the rapid cardiac pacing is introduced in the right ventricle.

The invention relates to the method for simulating heart failure in a conscious, instrumented animal as recited above, wherein the instrumented animal is selected from the group consisting of: pig, primate, including monkey and baboon, rabbit, cat, dog, sheep, goat, horse and cow.

The invention relates to the method for simulating heart failure in a conscious, instrumented animal as recited above, wherein the instrumented animal is mobile.

The invention relates to the method for simulating heart failure in a conscious, instrumented animal as recited above, wherein the instrumented animal is immobile.

The invention relates to the method for simulating heart failure in a conscious, instrumented animal as recited above, wherein the instrumented animal is a pig.

The invention relates to a method for simulating heart failure in an immobilized, conscious, instrumented pig comprising the steps of:

(a) inflating the distally implanted hydraulic occluder to occlude the distal left circumflex coronary artery about 7 to 10 days after the surgery to instrument the animal;

(b) waiting about 6 hours to 30 days after the distal left circumflex coronary artery occlusion; and (c) inflating the proximally implanted hydraulic occluder to occlude the proximal left circumflex coronary artery.

(d) waiting about 24 to about 48 hours after the proximal left circumflex coronary artery occlusion;

(e) using a cardiac pacemaker to introduce rapid cardiac pacing at a rate of about 190–210 beats/minute for about 1 to 7 days;

(f) waiting for about 0 to 72 hours after the first pacing; and (g) repeating steps (e) and (f) at least until the hemodynamic measurements, wherein hemodynamic measurements include: left atrial pressures; arterial pressure; aortic blood flow; total peripheral resistance; LV end-diastolic dimension; LV end systolic dimension; fractional shortening, mean velocity of circumferential fibre shortening and regional blood flows by radiolabeled microspheres; are indicative of heart failure.

The invention relates to the method for simulating heart failure in an immobilized, conscious, instrumented pig as recited above, which comprises introducing rapid cardiac pacing in the left or right ventricle.

The invention relates to the method for simulating heart failure in an immobilized, conscious, instrumented pig as recited above, which comprises introducing rapid cardiac pacing in the left or right atrium.

The invention relates to the method for simulating heart failure in an immobilized, conscious, instrumented pig as recited above, which comprises introducing rapid cardiac pacing in the right ventricle.

The invention relates to a method for assessing whether a test compound is therapeutically useful for the treatment of heart failure in an animal with simulated heart failure comprising the steps of:

(a) recording hemodynamic measurements, wherein hemodynamic measurements include: left atrial pressures; arterial pressure; aortic blood flow; total peripheral resistance; LV end-diastolic dimension; LV end systolic dimension; fractional shortening, mean velocity of circumferential fibre shortening and regional blood flows by radiolabeled microspheres; continuously before injection of the test compound in the animal with simulated heart failure;

(b) administering a dose of the test compound in the animal with simulated heart failure; and (c) recording hemodynamic measurements continuously for about 30 minutes to 6 weeks;

(d) repeating steps (a)–(c), administering a placebo dose in the animal with simulated heart failure as a control measurement; and (e) comparing the hemodynamic measurements of the test compound with the placebo control to determine if the hemodynamic burden on the heart and any associated congestion has been relieved by administration of the test compound.

The invention relates to the method for assessing whether a test compound is therapeutically useful for the treatment of heart failure in an animal with simulated heart failure as recited above, wherein the animal with simulated heart failure is selected from the group consisting of pig, primate, including monkey, baboon, rabbit, cat, dog, sheep, goat, horse and cow.

The invention relates to the method for assessing whether a test compound is therapeutically useful for the treatment of heart failure in an animal with simulated heart failure as recited above, wherein the method of administration of the test compound is selected from the group consisting of: oral, intravenous, intramuscular or subcutaneous, single and multiple doses.

The invention relates to the method for assessing whether a test compound is therapeutically useful for the treatment of heart failure in an animal with simulated heart failure as recited above, wherein the animal with simulated heart failure is mobile.

The invention relates to the method for assessing whether a test compound is therapeutically useful for the treatment of heart failure in an animal with simulated heart failure as recited above, wherein the hemodynamic measurements are recorded using instrumentation with telemetry.

The invention relates to the method for assessing whether a test compound is therapeutically useful for the treatment of heart failure in an animal with simulated heart failure as recited above, wherein the animal with simulated heart failure is immobile.

The invention relates to the method for assessing whether a test compound is therapeutically useful for the treatment of heart failure in an animal with simulated heart failure as recited above, wherein the method of administration of the test compound is oral or intravenous, single and multiple doses.

The invention relates to the method for assessing whether a test compound is therapeutically useful for the treatment of heart failure in an animal with simulated heart failure as recited above, wherein the method of administration of the test compound is oral, single and multiple doses.

The invention relates to the method for assessing whether a test compound is therapeutically useful for chronic treatment of heart failure in an animal with simulated heart failure as recited above, wherein the oral dose is about 0.1 $\mu$g/kg to 100 mg/kg, single and multiple doses.

The invention relates to the method for assessing whether a test compound is therapeutically useful for the treatment of heart failure in an animal with simulated heart failure as recited above, wherein the method of administration of the test compound is intravenous, single and multiple doses.

The invention relates to the method for assessing whether a test compound is therapeutically useful for the treatment of heart failure in an animal with simulated heart failure as recited above, wherein the intravenous dose is about 0.1 μg/kg to 10 mg/kg, single and multiple doses.

The invention relates to the method for assessing whether a test compound is therapeutically useful for the treatment of heart failure in an animal with simulated heart failure as recited above, wherein the animal with simulated heart failure is a pig.

The invention relates to the method for assessing whether a test compound is therapeutically useful for the treatment of heart failure in an animal with simulated heart failure as recited above, wherein the hemodynamic measurements are recorded continuously for about 30 minutes to 24 hours.

The invention relates to the method for assessing whether a test compound is therapeutically useful for the treatment of heart failure in an animal with simulated heart failure as recited above, wherein the hemodynamic measurements are recorded continuously for about 30 minutes to 8 hours.

The invention relates to the method for assessing whether a test compound is therapeutically useful for the treatment of heart failure in an animal with simulated heart failure as recited above, wherein the hemodynamic measurements are recorded continuously for about 90 minutes to 180 minutes.

The invention relates to a method for assessing whether a test compound is therapeutically useful for chronic treatment of heart failure in a conscious, instrumented animal comprising the steps of:

(a) administering the test compound to a conscious, instrumented animal prior to or during: (1) the production of myocardial ischemic injury and/or (2) the introduction of rapid cardiac pacing until the hemodynamic measurements are indicative of heart failure, wherein hemodynamic measurements include: left atrial pressures; arterial pressure; aortic blood flow; total peripheral resistance; LV end-diastolic dimension; LV end systolic dimension; fractional shortening, mean velocity of circumferential fibre shortening and regional blood flows by radiolabeled microspheres;

(b) recording the hemodynamic measurements continuously for about 30 minutes to 6 weeks of the conscious, instrumented animal;

(d) repeating steps (a)–(b), administering a placebo dose to a conscious, instrumented animal as a control measurement; and (e) comparing the hemodynamic measurements of the test compound with the placebo control to determine if the hemodynamic burden on the heart and any associated congestion has been relieved by administration of the test compound.

The invention relates to the method for assessing whether a test compound is therapeutically useful for chronic treatment of heart failure in a conscious, instrumented animal as recited above, wherein the animal is selected from the group consisting of pig, primate, including monkey and baboon, rabbit, cat, dog, sheep, goat, horse and cow.

The invention relates to the method for assessing whether a test compound is therapeutically useful for chronic treatment of heart failure in a conscious, instrumented animal as recited above, wherein the method of administration of the test compound is selected from the group consisting of: oral, intravenous, intramuscular or subcutaneous, single or multiple doses.

The invention relates to the method for assessing whether a test compound is therapeutically useful for chronic treatment of heart failure in a conscious, instrumented animal as recited above, wherein the animal with simulated heart failure is mobile.

The invention relates to the method for assessing whether a test compound is therapeutically useful for chronic treatment of heart failure in a conscious, instrumented animal as recited above, wherein the hemodynamic measurements are recorded using instrumentation with telemetry.

The invention relates to the method for assessing whether a test compound is therapeutically useful for chronic treatment of heart failure in a conscious, instrumented animal as recited above, wherein the animal with simulated heart failure is immobile.

The invention relates to the method for assessing whether a test compound is therapeutically useful for chronic treatment of heart failure in a conscious, instrumented animal as recited above, wherein the method of administration of the test compound is oral or intravenous, single or multiple doses.

The invention relates to the method for assessing whether a test compound is therapeutically useful for chronic treatment of heart failure in a conscious, instrumented animal as recited above, wherein the method of administration of the test compound is oral, single or multiple doses.

The invention relates to the method for assessing whether a test compound is therapeutically useful for chronic treatment of heart failure in a conscious, instrumented animal as recited above, wherein the oral dose is about 0.1 μg/kg to 100 mg/kg, single or multiple doses.

The invention relates to the method for assessing whether a test compound is therapeutically useful for chronic treatment of heart failure in a conscious, instrumented animal as recited above, wherein the method of administration of the test compound is intravenous, single or multiple doses.

The invention relates to the method for assessing whether a test compound is therapeutically useful for chronic treatment of heart failure in a conscious, instrumented animal as recited above, wherein the intravenous dose is about 0.1 μg/kg to 10 mg/kg, single or multiple doses.

The invention relates to the method for assessing whether a test compound is therapeutically useful for chronic treatment of heart failure in a conscious, instrumented animal as recited above, wherein the animal is a pig.

Figure 8:
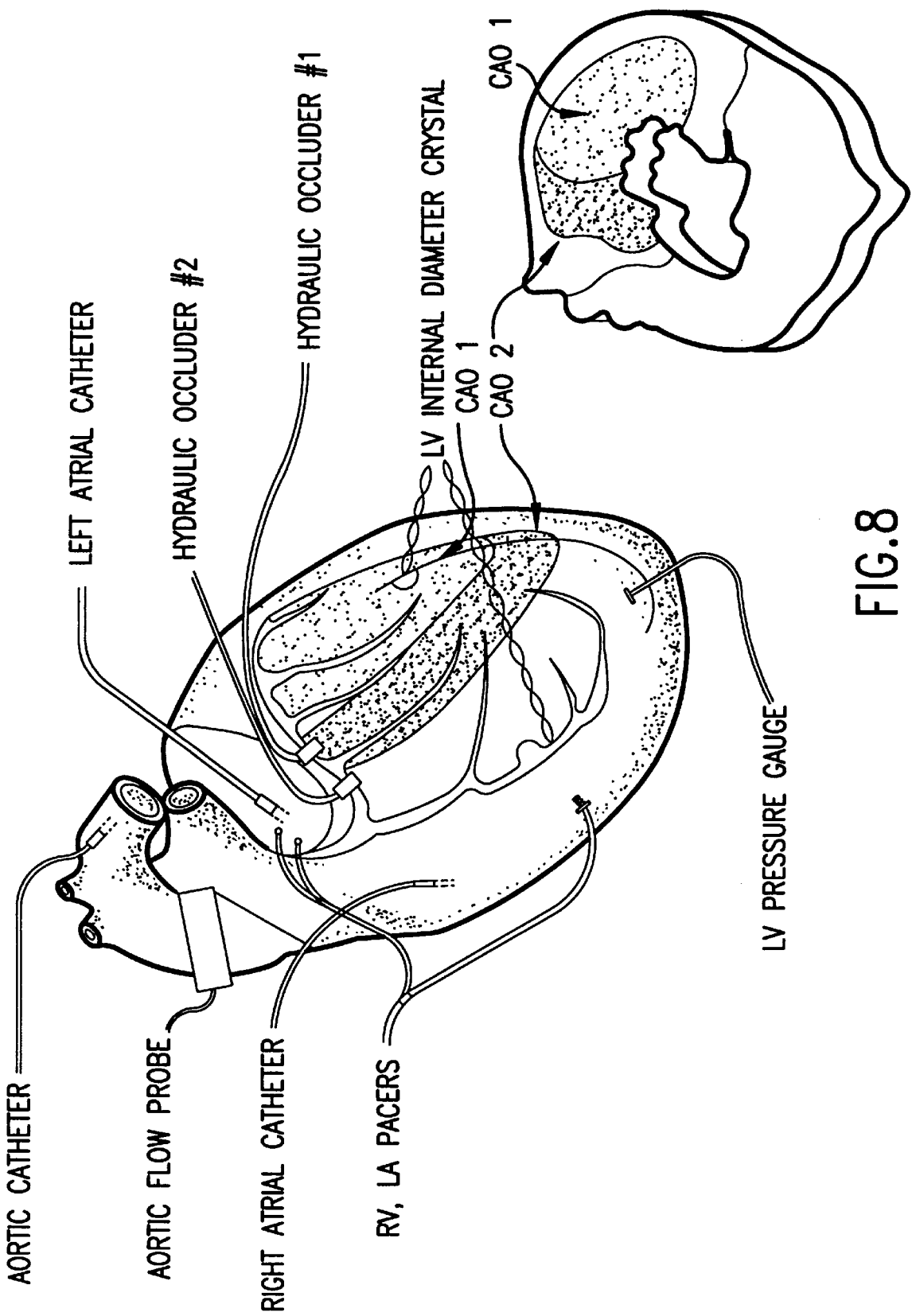
FIG. 8. Chronically instrumented heart failure model.

An instrumented animal is defined as an animal that has undergone surgery to implant the hardware necessary to induce heart failure and to obtain the hemodynamic measurements. The hemodynamic measurements include: left atrial pressures; arterial pressure; aortic blood flow; total peripheral resistance; LV end-diastolic dimension; LV end systolic dimension; fractional shortening and mean velocity of circumferential fibre shortening. Additionally, an echocardiogram can be utilized to measure the hemodynamic effects on the heart. The procedure described in Example 1 represents a method of instrumenting an animal, specifically a pig. FIG. 8 is a drawing of the instrumentation utilized in Example 1. This method of simulating heart failure is understood to include all known ways of producing myocardial ischemia including the coronary hydraulic occlusion procedure described in Example 1 and a microsphere microembolization procedure, preferably the coronary hydraulic occlusion procedure.

The rapid cardiac pacing is introduced using a cardiac pacemaker. The pacing can be done continuously or in cycles of 1 to 7 days with breaks of up to 72 hours at least until heart failure is evident. Heart failure is typically evident after 2 to 3 cycles of 7 days of rapid cardiac pacing with breaks of about 72 hours. Continous rapid cardiac pacing after heart failure is evident, is also within the scope of this invention.

In smaller "immobilized" animals (e.g. rabbit or cat in an activity box) in the absence of telemetry, one can record hemodynamics for 0.5–24 hours after dosing. With larger animals "immobilized" animals (e.g. dog, pig, primate, cow or horse) in a sling or chair in the absence of telemetry, one can record hemodynamics for 0.5–8 hours after dosing. The hemodynamic measurements can be recorded continuously using instrumentation with telemetry, for experiments set up to evaluate the effects of chronic treatment with a test compound on heart failure or the prevention of heart failure.

The animals can be instrumented such that they are mobile during the simulation of heart failure and during the adminstration of the test compound and hemodynamic measurements are recorded using instrumentation with telemetry. Alternatively, the animals are immobilized and hemodynamic measurements are recorded directly from the wire probes leading from the heart. The experiments carried out on immobilized animals are generally carried out over about 3 to 8 hours with hemodynamic measurements taken for upwards of 3 hours. The hemodynamic measurements can be recorded continuously for upwards of about 6 weeks with animals that are mobile using intrumentation with telemetry, for experiments set up to evaluate the effects of chronic treatment with a test compound on heart failure or the prevention of heart failure.

The test compound is administered in a pharmacologically effect dose range, and will depend on the potency of the individual test compound, the weight of the animals and the route of adminstration. The method of administration of the test compound includes: oral (p.o.), intravenous (i.v.), intramuscular (i.m.) or subcutaneous (s.c.). The preferred dose range would encompass about 0.1 $\mu$g/kg to 10 mg/kg i.v. or i.m. and about 0.1 $\mu$g/kg to 100 mg/kg p.o. or s.c. Test compounds could be administered as acute single doses (i.v., i.m., s.c. or p.o.) after the establishment of heart failure, or chronically with multiple doses (i.v., i.m., s.c. or p.o.) either after the establishment of heart failure or before the establishment of heart failure (even preceding surgical preparation, myocardial ischemia or rapid ventricular pacing) to assess the potential of the test compound to prevent heart failure. For purposes of comparision the instrumented animals are administered a placebo dose. The placebo dose comprising in the case of intravenous administration the vehicles used to solubilize the test compound or in the case of oral administration the binding agents used to formulate the test compound for oral administration.

The instant invention can be understood further by the following examples, which do not constitute a limitation of the invention.

EXAMPLE 1

Step A: Implantation of Instrumentation

Five farm pigs of either of sex and weighing 34.5±2.5 kg were sedated with ketamine hydrochloride (25 mg/kg, i.m.) and xylazine (6 mg/kg, i.m.). After tracheal intubation, general anesthesia was maintained with isoflurane (1.5–2.0 vol % in oxygen). Using sterile surgical technique, a left thoracotomy was performed at the fifth intercostal space. Catheters made of Tygon tubing (Norton Performance Plastics Co., Akron, Ohio) were implanted in the descending aorta, left and right atria for measurement of pressures. A solid-state miniature pressure gauge (Konigsberg Instruments Inc., Pasadena, Calif.) was implanted in the left ventricular (LV) chamber to obtain LV pressure and the rate of change of LV pressure (LV dP/dt). A flow probe (Transonic System Inc., Ithaca, N.Y.) was placed around the main pulmonary artery for measurement of blood flow. One pair of piezoelectric ultrasonic dimension crystals were implanted on opposing anterior and posterior endocardial regions of the LV to measure the short-axis internal diameter. Proper alignment of the endocardial crystals was achieved during surgical implantation by positioning the crystals so as to obtain a signal with the greatest amplitude and shortest transit time. A pacing lead (model 5069, Medtronic Inc., Minneapolis, Minn.) was attached to the right ventricular free wall, and stainless steel pacing leads were attached to the left atrial appendage. The left circumflex coronary artery was isolated and two hydraulic occluders, made of Tygon tubing, were implanted proximally and distally to the first obtuse marginal branch. The wires and catheters were externalized between the scapulae, the incision was closed in layers, and air was evacuated from the chest cavity. See FIG. 8.

Step B: Experimental Measurements

Hemodynamic recordings were made using a data tape recorder (RD-130TE, TEAC, Montebello, Calif.) and a multiple-channel oscillograph (MT95K2, Astro-Med, West Warwick, R.I.). Aortic and left atrial pressures were measured using strain gauge manometers (Statham Instruments, Oxnard, Calif.), which were calibrated in vitro using a mercury manometer, connected to the fluid-filled catheters. The solid-state LV pressure gauge was cross-calibrated with aortic and left atrial pressure measurements. LV dP/dt was obtained by electronically differentiating the LV pressure signal. Blood flow was measured using a volume flow meter (T208, Transonic System Inc., Ithaca, N.Y.). Mean arterial pressure, left atrial pressures, and pulmonary blood flow (cardiac output) were measured using an amplifier filter. Stroke volume was calculated as the quotient of cardiac output and heart rate. Cardiac output was normalized by body weight to yield cardiac index. LV dimension was measured with an ultrasonic transit-time dimension gauge (Model 203, Triton Technology Inc., San Diego, Cailf.). Total peripheral resistance was calculated as the quotient of mean arterial pressure and cardiac output. LV short-axis end-diastolic dimension (EDD) was measured at the beginning of the upstroke of the LV dP/dt signal. LV end-systolic dimension (ESD) was measured at the time of maximum negative dP/dt. The percent shortening of LV internal diameter was calculated as (EDD-ESD)/EDD*100. LV mean velocity of circumferential fibre shortening (Vcf) was calculated from the dimension measurements using the following formula:(EDD-ESD)/EDD/Ejection time ($sec^{-1}$). Ejection time was measured as the interval between maximum and minimum LV dP/dt. A cardiotachometer triggered by the LV pressure pulse provided instantaneous and continuous records of heart rate.

Step C: Heart Failure Model

Experiments were initiated 10–14 days after surgery, when the pigs were fully recovered from surgery. During the post-operative period, the pigs were introduced to a sling for training. Heart failure was produced by progressive myocardial ischemia induced by two coronary artery occlusions followed by intermittent ventricular pacing. Briefly, after post-surgical hemodynamic control monitoring was performed, the left circumflex coronary artery was occluded by inflating the distally implanted hydraulic occluder. Approximately 48 hrs after the first occlusion, the proximal coronary artery occluder was inflated. One to two days following the second myocardial infarction, the right ventricle was paced at a rate of 190–210 beats/min using a programmable external cardiac pacemaker (model EV4543, Pace Medical, Waltham, Mass.). Pacing was continued for 1 week and then terminated for 3 days. This procedure was repeated another 1–2 cycles, until heart failure was evident and the hemodynamic parameters were stable.

Step D: Experimental Protocols

Hemodynamic experiments were performed after 2 cycles of tachycardic pacing in the presence of myocardial ischemia injury, after the animal had achieved a stable state of heart failure. During the experiments, the pigs were conscious and quietly restrained in a sling. The test compound is dissolved in saturated NaHCO$_3$ (10% by Vol) and 0.9% saline (90% by Vol) at a concentration of 2 mg/ml, was studied in four conscious pigs with heart failure. A dose of 0.5 mg/kg was injected intravenously over a period of 2 minutes, and hemodynamics were continuously recorded before and 90 minutes following injection of the test compound in all 4 pigs. In two of these pigs, recording continued until 3 hours following injection of the test compound. The vehicle was tested on separate days. The effects of 0.1 to 0.5 μg/kg cumulative bolus doses in 0.1 μg/kg steps of endothelin-1 (Peptide Institute, Inc., Osaka, Japan) were also examined on separate days before and 90 minutes after injection of the test compound in three pigs during development of heart failure to characterize the extent of endothelin block by the test compound. ET-1 was dissolved in 0.1 N NaHCO$_3$ (95% by Vol) and 0.9% saline (95% by Vol) at a concentration of 20 μg/ml.

Step E: Data Analysis

All data were stored on an AST 4/d computer. Data before and after development of heart failure were compared using Student's t-test for paired data. The data at baseline and after injection of the test compound also were compared using Student's t-test for paired data with a Bonferroni correction. All values are expressed as the mean±S.E. Statistical significance was accepted at the $p<0.05$ level.

EXAMPLE 2

Experimental Protocol Using an Endothelin Antagonist: Compound 1

Step A: Hemodynamic Study with Compound 1

Hemodynamic experiments were performed after 2 cycles of tachycardic pacing in the presence of myocardial ischemia injury, after the animal had achieved a stable state of heart failure. During the experiments, the pigs were conscious and quietly restrained in a sling. Compound 1, ((+)-(5S*, 6R*, 7R*)-2-butyl-6-carboxy-7-[2-(2-carboxypropyl)-4-methoxyphenyl]-5-(3,4-methylenedioxyphenyl)-cyclopenteno[1,2-b]pyridine), dissolved in saturated NaHCO$_3$ (10% by Vol) and 0.9% saline (90% by Vol) at a concentration of 2 mg/ml, was studied in four conscious pigs with heart failure. A dose of 0.5 mg/kg was injected intravenously over a period of 2 minutes, and hemodynamics were continuously recorded before and 90 minutes following injection of Compound 1 in all 4 pigs. In two of these pigs, recording continued until 3 hours following injection of Compound 1. The vehicle was tested on separate days. The effects of 0.1 to 0.5 μg/kg cumulative bolus doses in 0.1 μg/kg steps of endothelin-1 (Peptide Institute, Inc., Osaka, Japan) were also examined on separate days before and 90 minutes after injection of Compound 1 in three pigs during development of heart failure to characterize the extent of ET block by Compound 1. ET-1 was dissolved in 0.1 N NaHCO$_3$ (95% by Vol) and 0.9% saline (95% by Vol) at a concentration of 20 μg/ml. For comparative purpose, the effects of intravenous injection of Compound 2(enalaprilat), at doses of 1 mg/kg and 4 mg/kg, were studied on different days in three of the pigs that were used to study Compound 2 and in one additional pig. Compound 2 was dissolved in 0.9% saline.

Step B: Baseline Hemodynamics Before and After Development of Heart Failure

Tables 1 and 2 summarize the baseline LV function and systemic vascular dynamics before (i.e., post surgical control) and after heart failure induced by serial myocardial infarctions in combination with intermittent tachycardic stress in conscious pigs. Heart failure resulting from at least 2 cycles of tachycardic pacing in the presence of myocardial injury was manifested by significant increases in LV end-diastolic (+10.7±0.4 mm from 40.2±3.6 mm) and end-systolic diameters (+14.6±1.1 mm from 31.2±2.7 mm) and in mean left atrial pressure (+19±3 mmHg from 4±2 mmHg). LV dP/dt, LV fractional shortening, Vcf, and cardiac index significantly decreased by 45±4, 54±6, 46±1 and 29±8%, respectively. Also, total peripheral resistance increased significantly (+46±14%), while mean arterial pressure and heart rate were unchanged. In addition to these hemodynamic changes, which are shown in FIGS. 1 and 2, heart failure, particularly at the advanced stages, was characterized by anorexia, peripheral and pulmonary edema, and reduced activity.

TABLE 1

Baseline Left Ventricular Function in Controls and Conscious Pigs with Heart Failure.

| | Control | Heart Failure |
|---|---|---|
| LV End-Diastolic Diameter (mm) | 40.2 ± 3.6 | 50.9 ± 3.5* |
| LV End-Systolic Diameter (mm) | 31.2 ± 2.7 | 45.8 ± 3.6* |
| LV Fractional Shortening (%) | 22.3 ± 1.5 | 10.3 ± 1.3* |
| Vcf (sec$^{-1}$) | 1.1 ± 0.1 | 0.6 ± 0.0* |
| LV dP/dt (mmHg/sec) | 3012 ± 153 | 1681 ± 184* |

*Significantly different from control, $p<0.05$.
Data are mean ± SE with n = 3, except that LV dP/dt n = 4.

TABLE 2

Baseline Cardiac and Systemic Hemodynamics in Controls and Conscious Pigs with Heart Failure.

| | Control | Heart Failure |
|---|---|---|
| Mean Arterial Pressure (mmHg) | 90 ± 3 | 88 ± 5 |
| Mean Left Atrial Pressure (mmHg) | 4 ± 2 | 23 ± 3* |
| Cardiac Index (ml/min/kg) | 123 ± 11 | 86 ± 9* |
| Total Peripheral Resistance (mmHg/ml/min/kg) | 0.73 ± 0.06 | 1.04 ± 0.09* |
| Heart Rate (beat/min) | 139 ± 4 | 143 ± 15 |

*Significantly different from control, $p<0.05$.
Data are mean ± SE with n = 4.

Step C: Effects of Compound 1 on Hemodynamics in Heart Failure

The time course of hemodynamic changes following intravenous administration of Compound 1 (0.5 mg/kg) are shown in FIGS. 3 and 4 Tables 3 and 4 summarize LV function and systemic hemodynamic responses to Compound 1 at 15 minutes and 60 minutes after administration of Compound 1. FIGS. 1 and 2 illustrate the cardiac and systemic dynamic measurements made before and after development of heart failure, as well as 60 minutes after administration of Compound 1 during the heart failure stage.

Compound 1 mainly induced a sustained increase in cardiac index, and prolonged decreases in mean arterial pressure and total peripheral resistance. For example, at 60 minutes after administration of Compound 1, mean arterial pressure was significantly decreased by 10±2% and cardiac index was increased by 17±4%. Thus, total peripheral resistance was significantly decreased by 22±3% with Compound 1, which basically constitutes a complete restoration of the elevated vascular resistance of heart failure back to pre-heart failure control values (FIG. 1). Although Compound 1 also decreased left atrial pressure and increased heart rate, these changes were not statistically significant.

Vcf was increased by 12±2%, while LV dP/dt, LV end-diastolic and systolic diameter, and LV fraction shortening were not affected by Compound 1. The vehicle did not induce any significant changes throughout 180 minutes of observation (FIGS. 3 and 4).

The salutary effects of acute administration of Compound 1 in this heart failure model were predominantly due to the reversal of elevated vascular resistance.

TABLE 3

Effects of Intravenous Injection of Compound 1 (0.5 mg/kg) on LV Function in Conscious Pigs with Heart Failure.

|  | Baseline | Change from Baseline | |
| --- | --- | --- | --- |
|  |  | 15 min | 60 min |
| LV End-Diastolic Diameter (mm) | 50.9 ± 3.5 | +0.1 ± 0.2 | +0.2 ± 0.3 |
| LV End-Systolic Diameter (mm) | 45.8 ± 3.6 | −0.3 ± 0.3 | −0.2 ± 0.3 |
| LV Fractional Shortening (%) | 10.3 ± 1.3 | +0.6 ± 0.2 | +0.7 ± 0.2 |
| Vcf (sec$^{-1}$) | 0.60 ± 0.04 | 0.05 ± 0.01* | +0.07 ± 0.02* |
| LV dP/dt (mmHg/sec) | 1681 ± 184 | +25 ± 40 | +56 ± 65 |

*Significantly different from baseline, p<0.025.
Data are mean ± SE with n = 3, except that LV dP/dt n = 4.

TABLE 4

Effects of Intravenous Injection of Compound 1 (0.5 mg/kg) on Cardiac and Systemic Hemodynamics in Conscious Pigs with Heart Failure.

|  | Baseline | Change from Baseline | |
| --- | --- | --- | --- |
|  |  | 15 min | 60 min |
| Left Atrial Pressure (mmHg) | 23 ± 3 | −4 ± 2 | −2 ± 2 |
| Mean Arterial Pressure (mmHg) | 88 ± 5 | −10 ± 1* | −8 ± 1* |
| Cardiac Index (ml/min/kg) | 86 ± 9 | +14 ± 2* | +13 ± 2* |
| Total Peripheral Resistance (mmHg/ml/min/kg) | 1.04 ± 0.09 | −0.25 ± 0.03* | −0.24 ± 0.05 |
| Heart Rate (beat/min) | 143 ± 15 | +5 ± 5 | +7 ± 5 |

*Significantly different from baseline, p<0.025.
Data are mean ± SE with n = 4.

Step D: Effects of Compound 1 Compared with Compound 2 in Heart Failure

Figure 6:
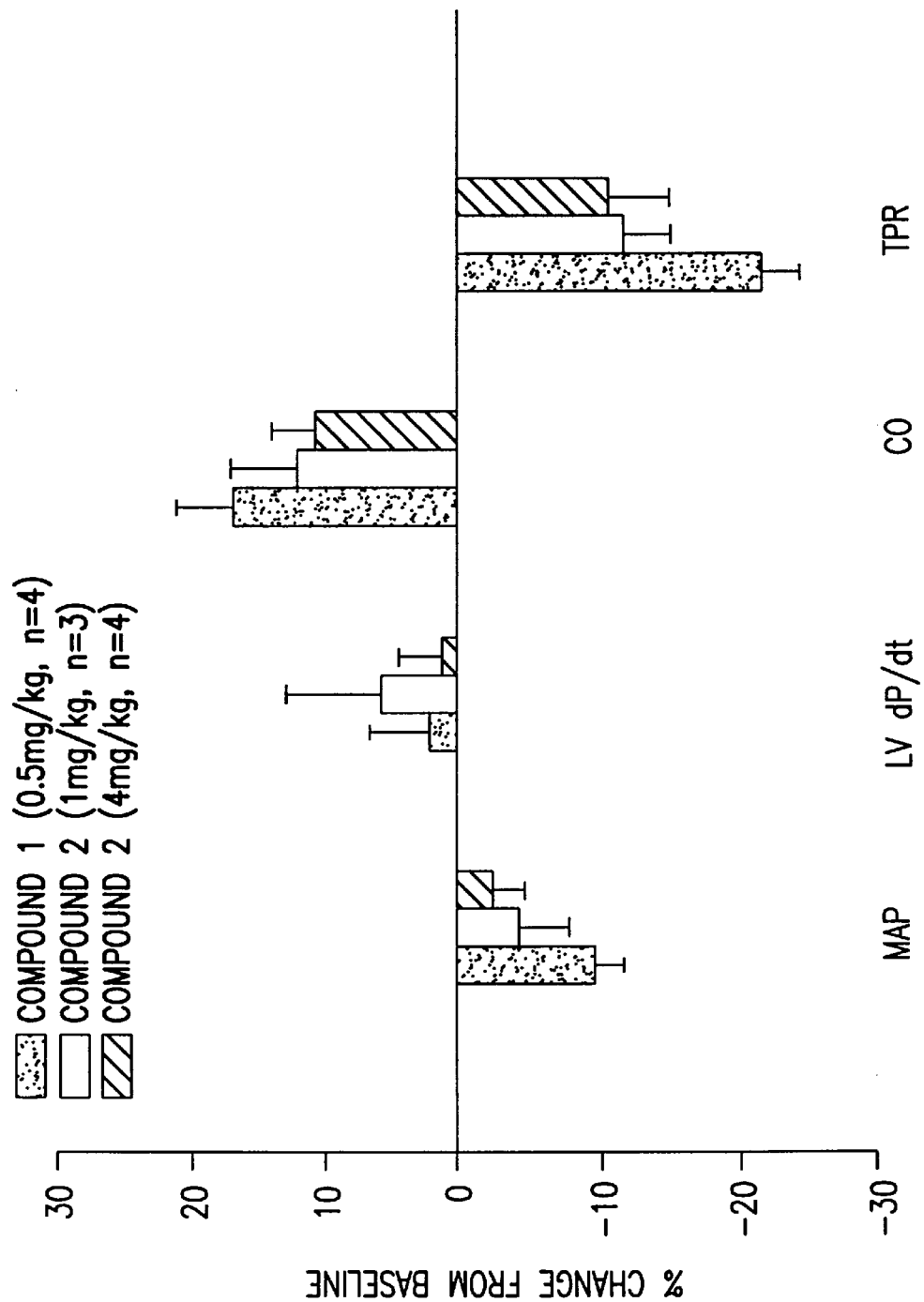
FIG. 6. Comparison of the mean arterial pressure (MAP), LV dP/dt, cardiac output (CO) and total peripheral resistance (TPR) responses at 60 min after injection of Compound 1 (0.5 mg/kg, i.v.) or Compound 2 (1 mg/kg and 4 mg/kg, i.v.) in conscious pigs after development of heart failure. Values are expressed as the percent changes from baseline levels. Data are mean±SE and the number of animals studied is in parenthesis.
Figure 7A:
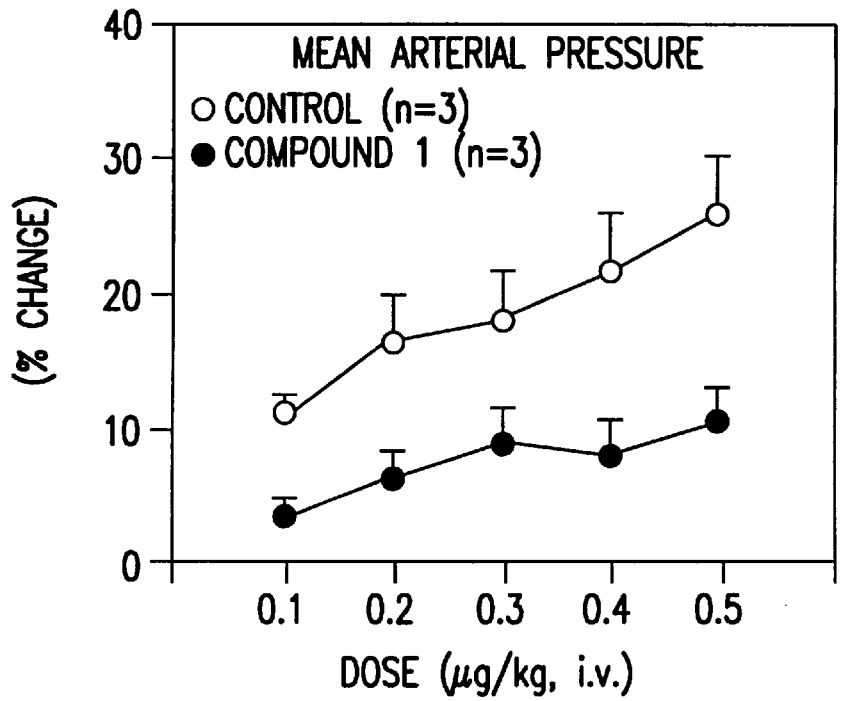
FIG. 7. Effects of endothelin-1 (ET-1, 0.1 to 0.5 μg/kg, i.v.) on mean arterial pressure, mean left arterial pressure, total peripheral resistance and heart rate in conscious pigs after development of heart failure with and without Compound 1 (0.5 mg/kg, i.v.). Values are expressed as the percent changes from baseline levels, except mean left atrial pressure which is change from baseline value in mmHg. Data are mean±SE and the number of animals studied is in parenthesis.
Figure 7B:
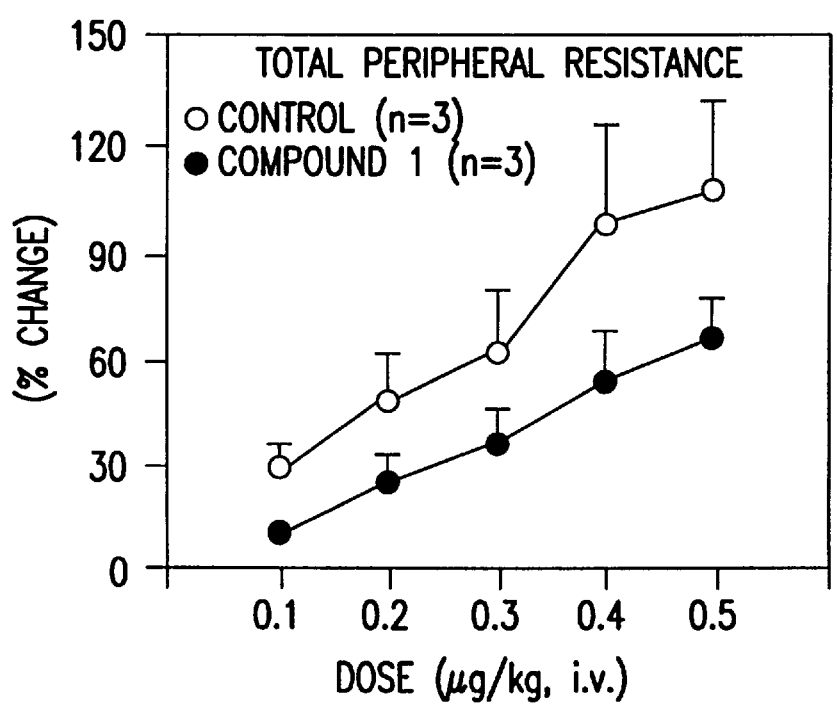
Figure 7C:
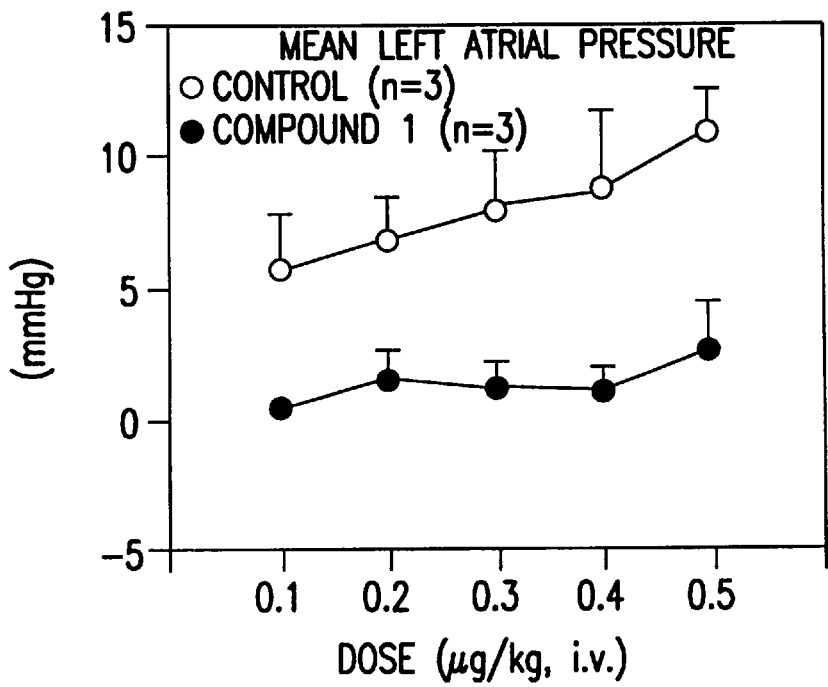
Figure 7D:
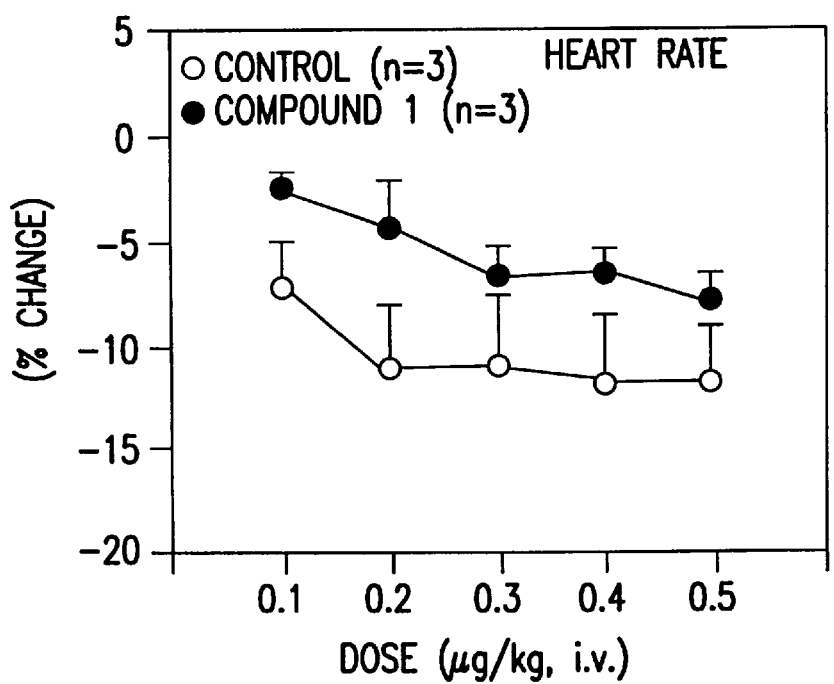

FIG. 5 compares the effects of intravenous administration of Compound 1 (0.5 mg/kg) and Compound 2 (enalaprilat) (1 mg/kg or 4 mg/kg) on total peripheral resistance in conscious pigs with heart failure. While the effects were not dose-dependent, suggesting maximal effect, both doses of Compound 2 did significantly reduce the total peripheral resistance to a similar level throughout 90-minute observation period. The reduction in total peripheral resistance by administration of Compound 1 (0.5 mg/kg) was greater than that induced by either dose of Compound 2. FIG. 6 compares the changes in mean arterial pressure, LV dP/dt, cardiac output and total peripheral resistance at 60 minutes after administration of Compound 1 or Compound 2.

Step E: Effects of ET-1 in the Absence and Presence of Compound 1 in Heart Failure FIG. 7 shows the effects of cumulative intravenous bolus injections of ET-1 (total dose of 0.5 µg/kg) on mean arterial pressure, mean left atrial pressure, total peripheral resistance and heart rate before and after intravenous administration of Compound 1 at a dose of 0.5 mg/kg. ET-1 induced significant dose-dependent increases in mean arterial pressure, mean left atrial pressure and total peripheral resistance. Heart rate decreased, but not dose-dependently. The hemodynamic responses to ET-1 were markedly attenuated after administration of Compound 1, suggesting the 0.5 mg/kg, i.v. dose of Compound 1 to be capable of significant blocking the effects of exogenous ET-1.

Compound 1, at a dose of 0.5 mg/kg, i.v. reduced the elevated vascular resistance but did not affect myocardial contractility in conscious pigs with heart failure. This acute effect of Compound 1 was greater than that of 1 mg/kg or 4 mg/kg, i.v. Compound 2. The salutary effects of Compound 1 in this heart failure model were attributed to ET receptor antagonism since the hemodynamic responses to an ET-1 challenge were markedly attenuated by the same dose of Compound 1.

EXAMPLE 3

Experimental Protocol Using an Angiotensin Converting Enzyme Inhibitor and an Angiotensin II Antagonist—Compound 2 and Compound 3

Step A: Hemodynamic Study with ACEI-AII Combination

Hemodynamic experiments were performed after 2 cycles of tachycardiac pacing in the presence of myocardial ischemic injury, after the animal had achieved a stable state of heart failure. During the experiments, the pigs were conscious and quietly restrained in a sling. The following eight treatment regimens (groups) were studied on different days:

1) Compound 2 (enalaprilat) (1 mg/kg, n=3).
2) Compound 3 (3-[(2'-tetrazol-5-yl)biphenyl-4-yl]methyl-5,7-dimethyl-2-ethyl-3H-imidazo[4,5-b]pyridine) (1 mg/kg, n=4).
3) Compound 2 (1 mg/kg) followed by a dose of Compound 3 (1 mg/kg, n=5).
4) Compound 2 (1 mg/kg) followed by a second dose of Compound 2 (1 mg/kg, n=4).
5) Compound 2 (1 mg/kg) and Compound 3 concomitantly (1 mg/kg, n=4).
6) Compound 2 at high dose (4 mg/kg, n=4).
7) Compound 3 at high dose (4 mg/kg, n=3).
8) Vehicle (n=4).

For groups 3 and 4 above, the additional doses of either Compound 3 or Compound 2 were administered 30 min after the first dose. Compound 2 was dissolved in 0.9% saline, and Compound 3 was dissolved in saturated NaHCO$_3$ (10% by Vol) and 0.9% saline (90% by Vol) at a concentration of 2 mg/ml. Hemodynamic measurements were continuously recorded before and for 90 min after intravenously injecting each of the treatment or the vehicle over a 2-min period.

Step B: Baseline Hemodynamics Before and After Development of Heart Failure

Figure 9:
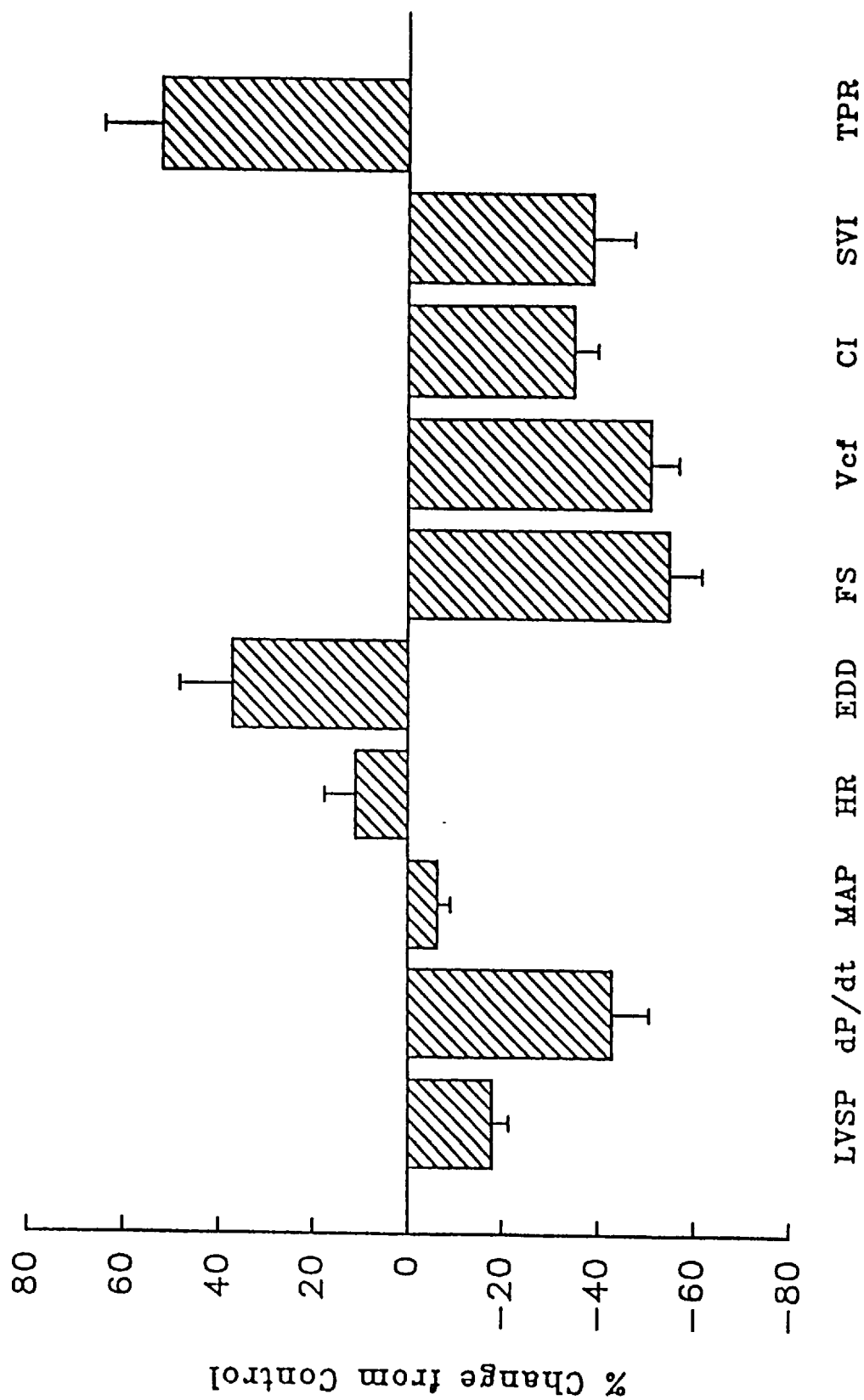
FIG. 9. Percent change in LV systolic pressure (LVSP), LV dP/dt, mean arterial pressure (MAP), heart rate (HR), LV end-diastolic dimension (EDD), LV fractional shortening (FS), mean velocity of circumferential fibre shortening (Vcf), cardiac index (CI), stroke volume index (SVI) and total peripheral resistance (TPR) from the control in 6 conscious pigs after developing heart failure.
Figure 10A:
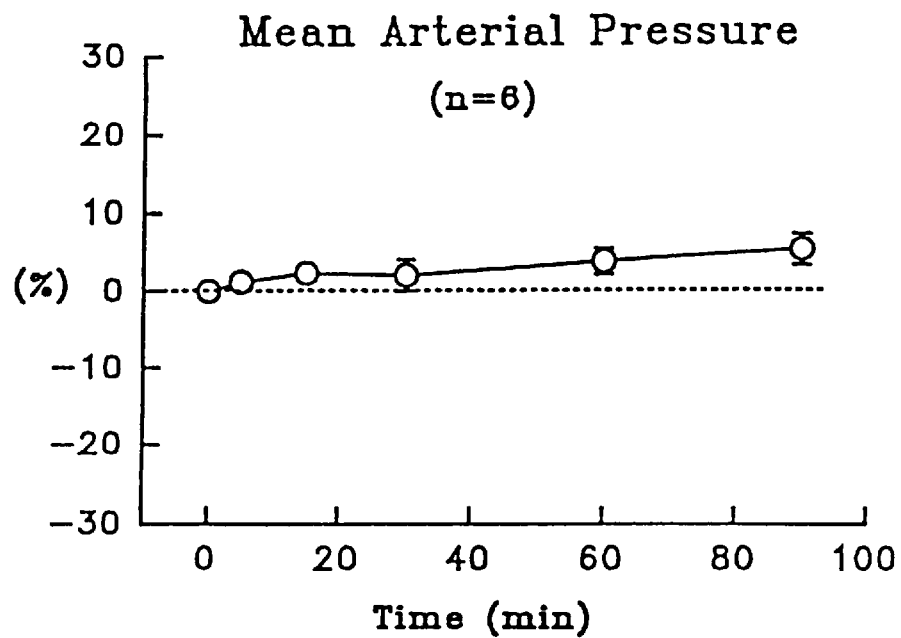
FIG. 10. Effects of vehicle on mean arterial pressure, total peripheral resistance, LV dP/dt, and Vcf in conscious pigs with heart failure. Values (mean±SE) are expressed as percent change from baseline.
Figure 10B:
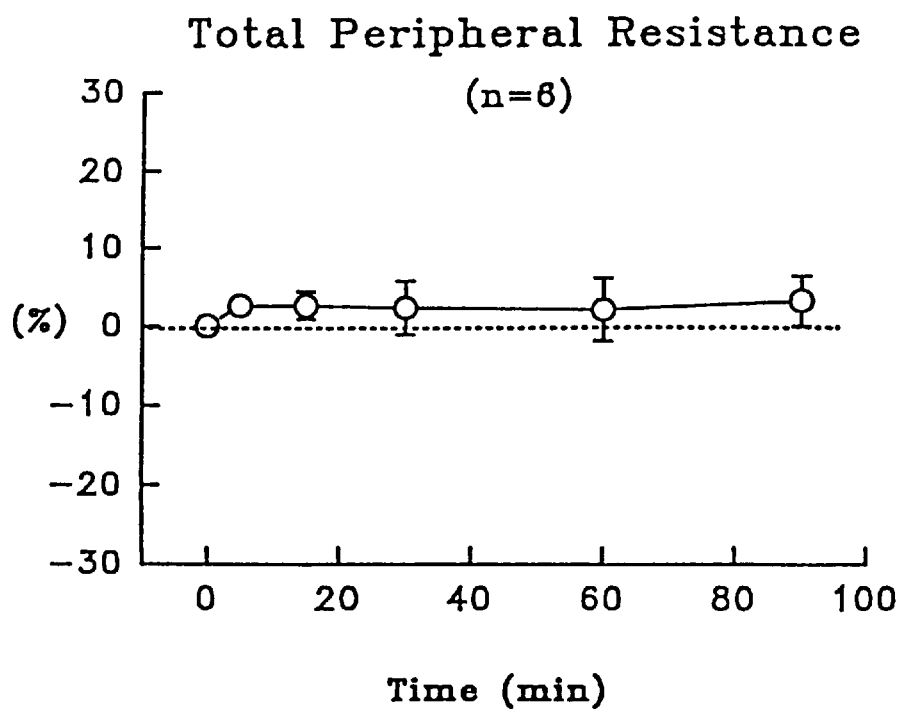
Figure 10C:
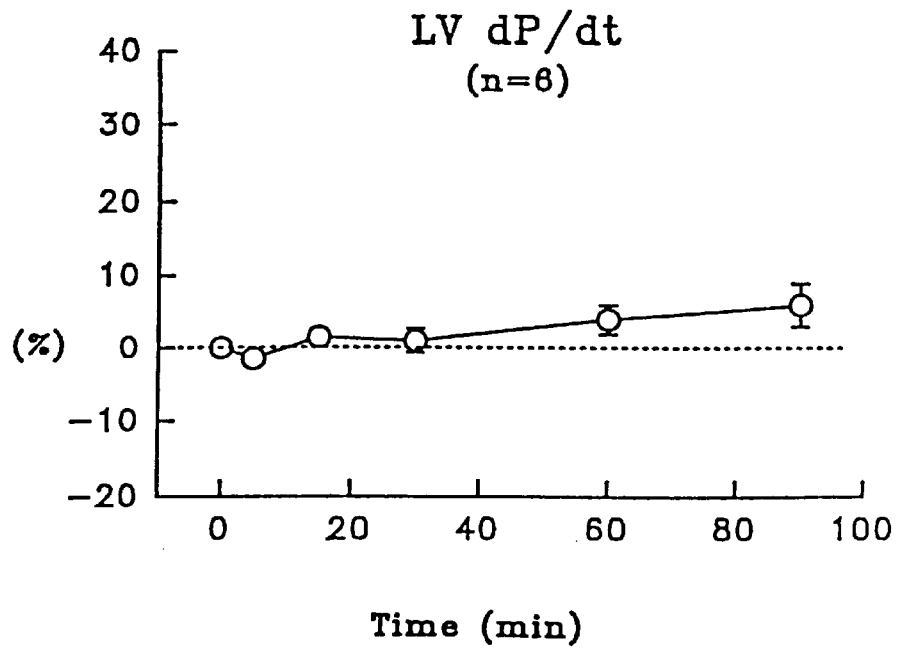
Figure 10D:
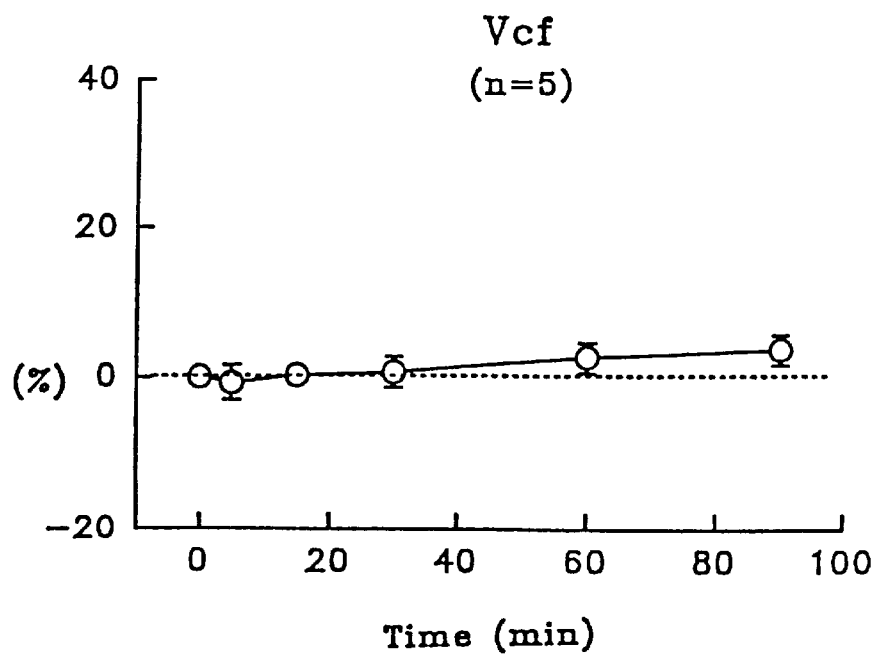
Figure 11A:
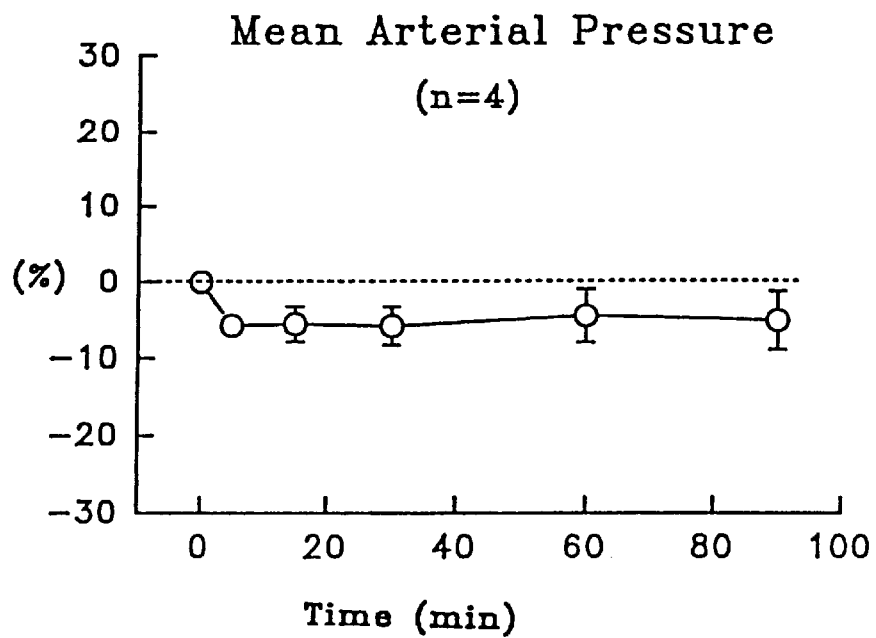
FIG. 11. Effects of Compound 2 (1 mg/kg, i.v.) on mean arterial pressure, total peripheral resistance, LV dP/dt, and Vcf in conscious pigs with heart failure. Values (mean±SE) are expressed as percent change from baseline.
Figure 11B:
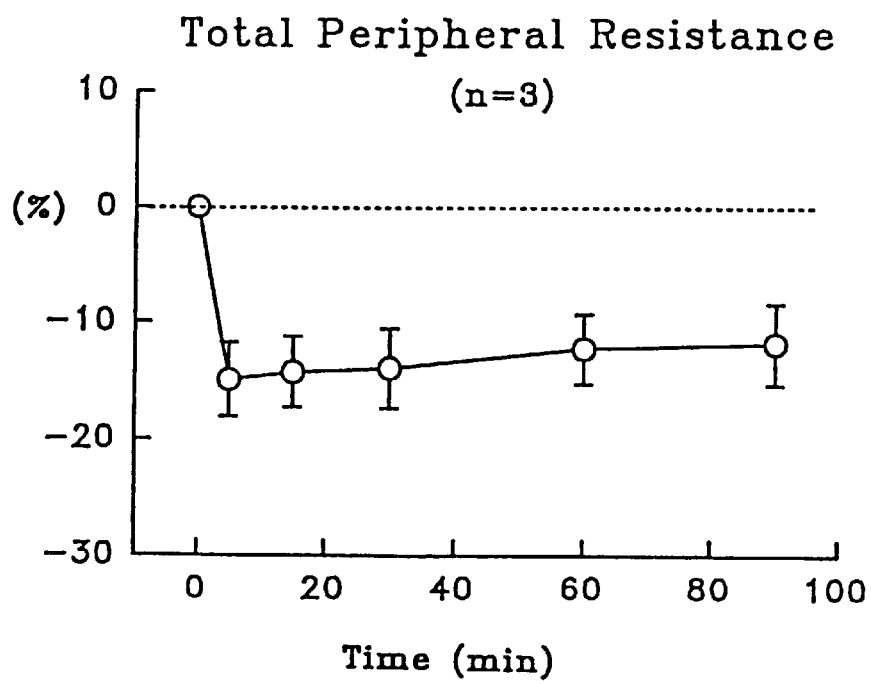
Figure 11C:
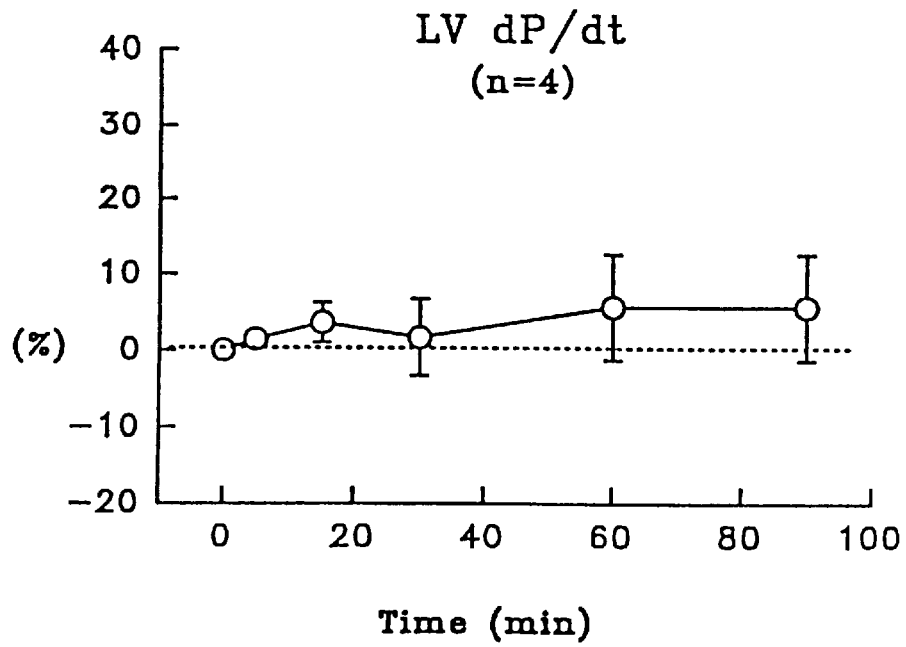
Figure 11D:
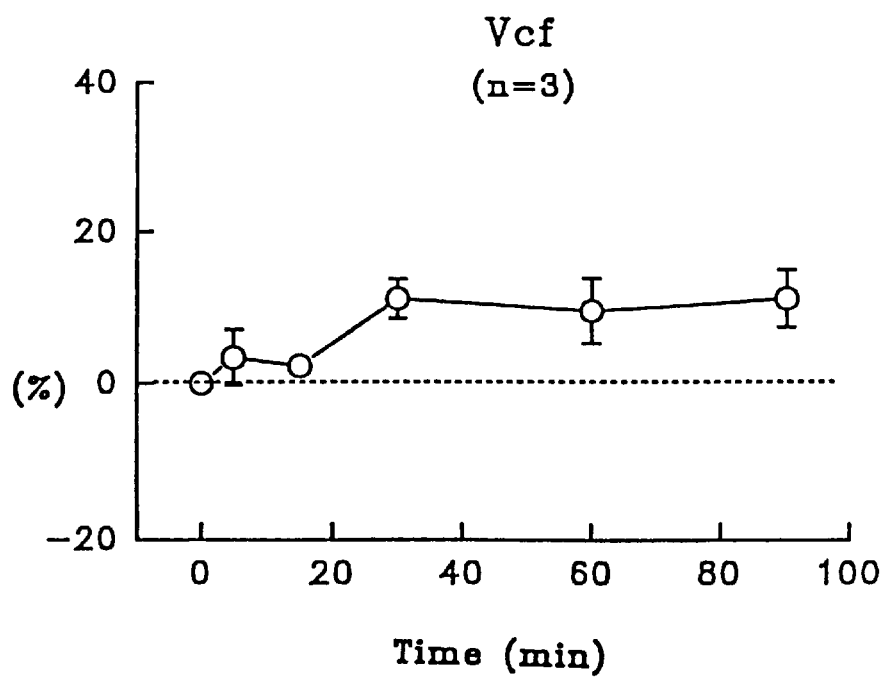
Figure 12:
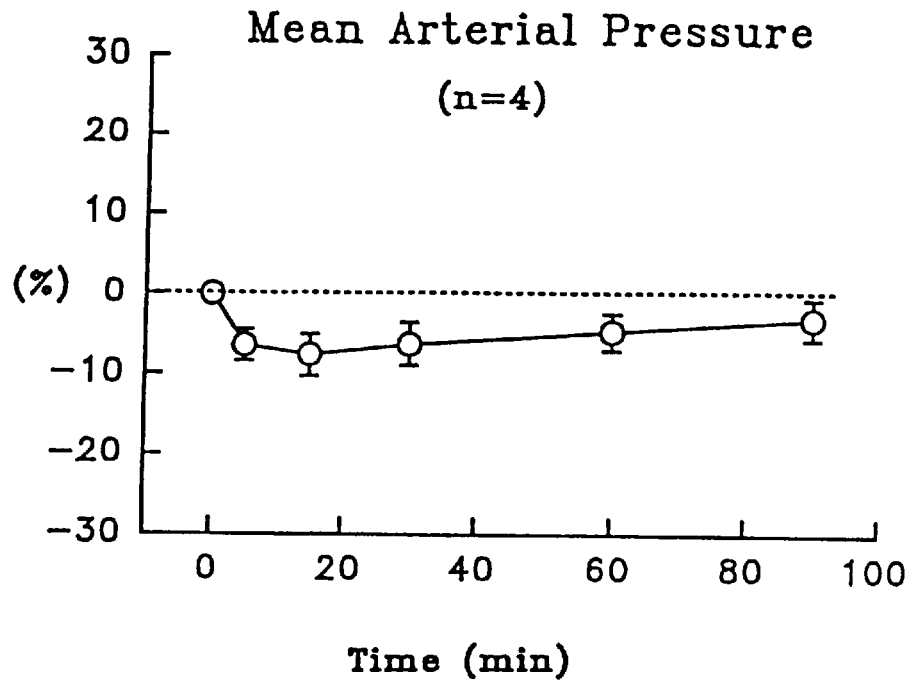
FIG. 12. Effects of Compound 3 (1 mg/kg, i.v.) on mean arterial pressure, total peripheral resistance, LV dP/dt, and Vcf in conscious pigs with heart failure. Values (mean±SE) are expressed as percent change from baseline.
Figure 12:
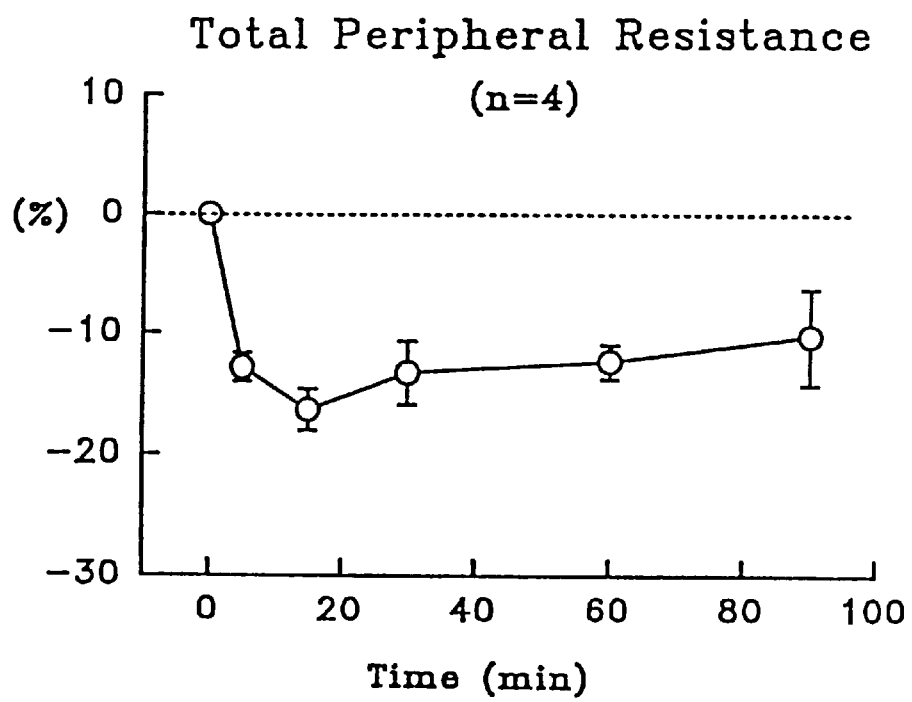
Figure 12C:
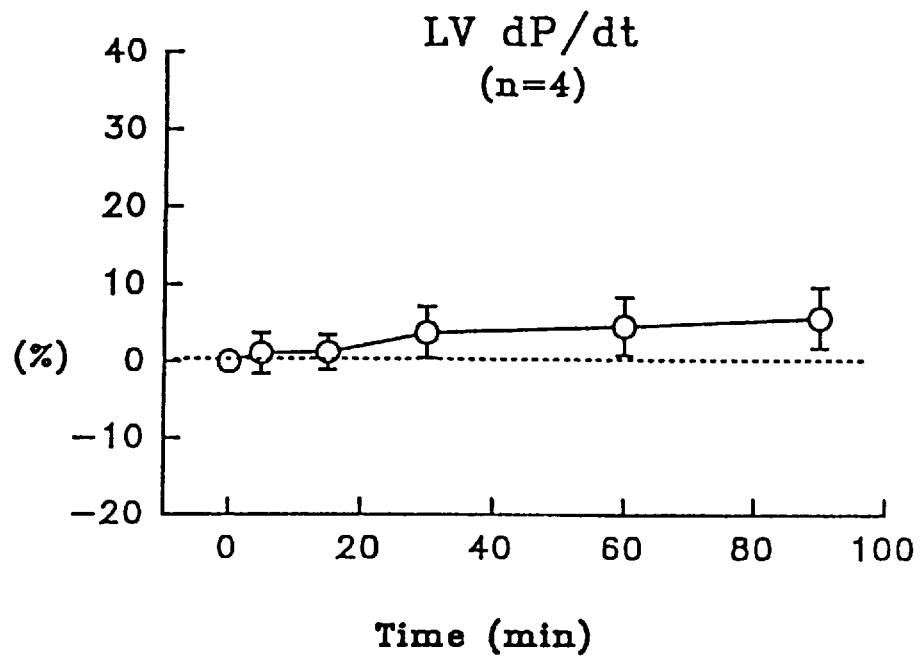
Figure 12D:
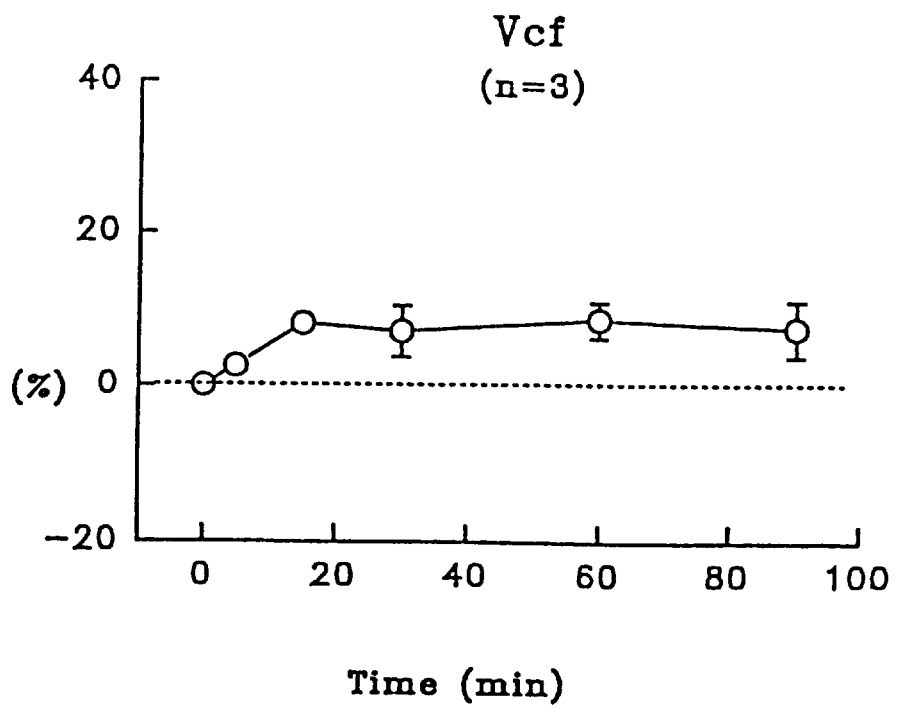
Figure 13A:
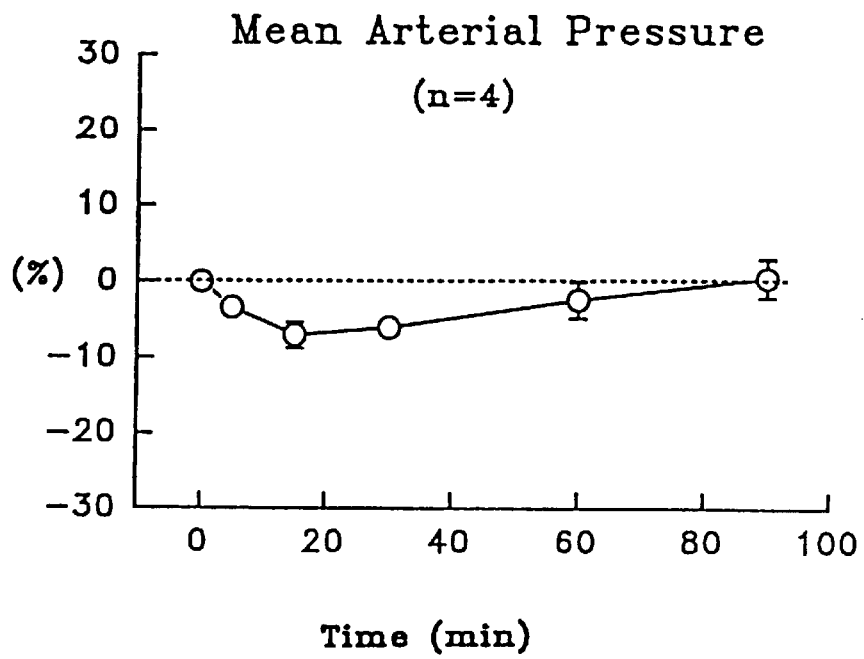
FIG. 13. Effects of Compound 2 (4 mg/kg, i.v.) on mean arterial pressure, total peripheral resistance, LV dP/dt, and Vcf in conscious pigs with heart failure. Values (mean±SE) are expressed as percent change from baseline.
Figure 13B:
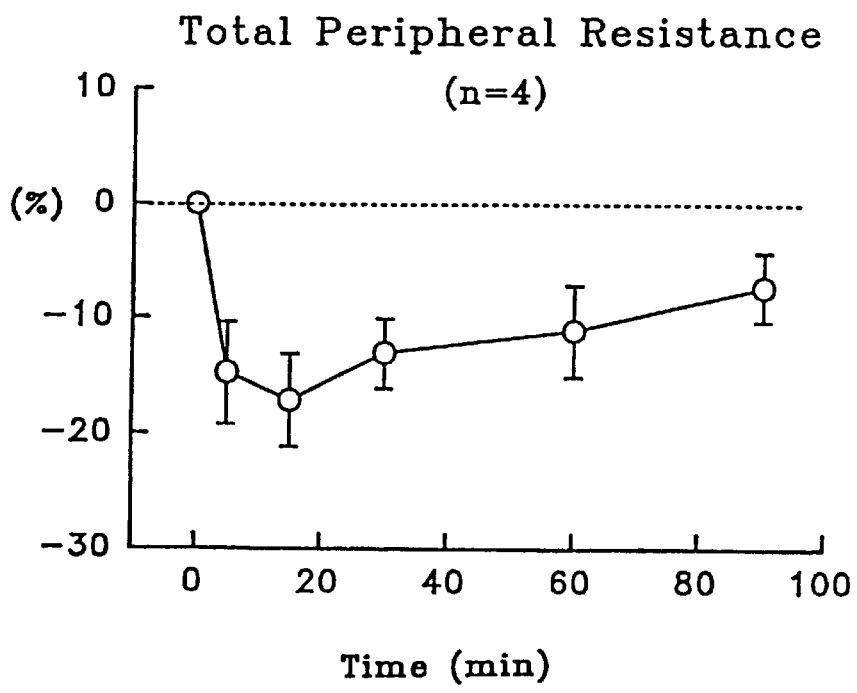
Figure 13C:
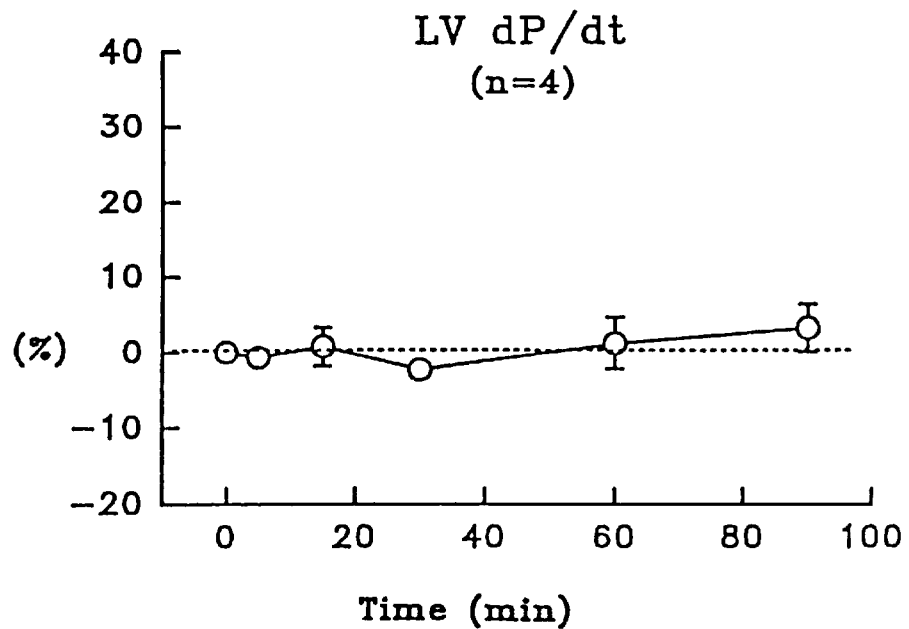
Figure 13D:
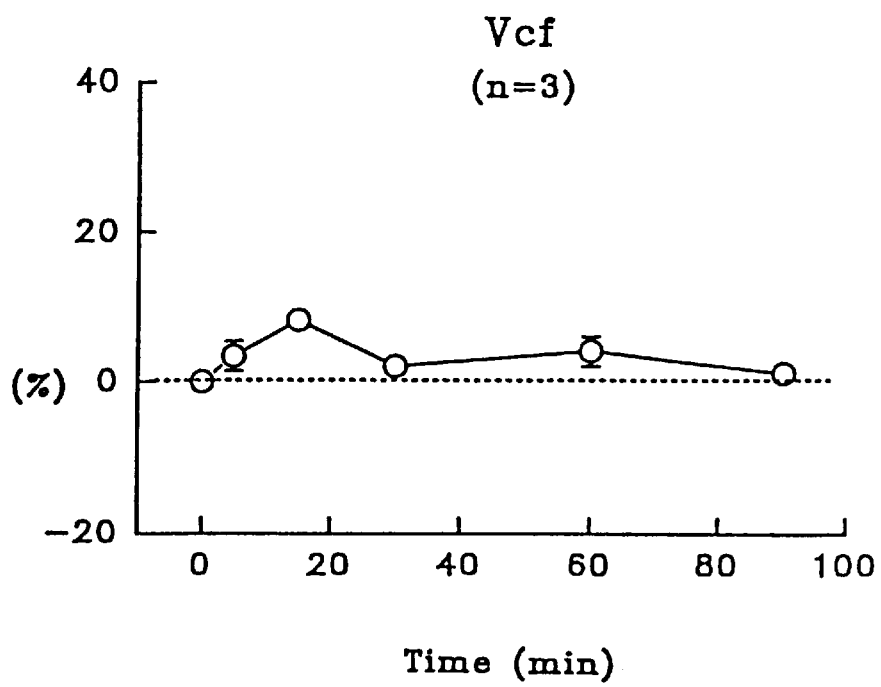
Figure 14A:
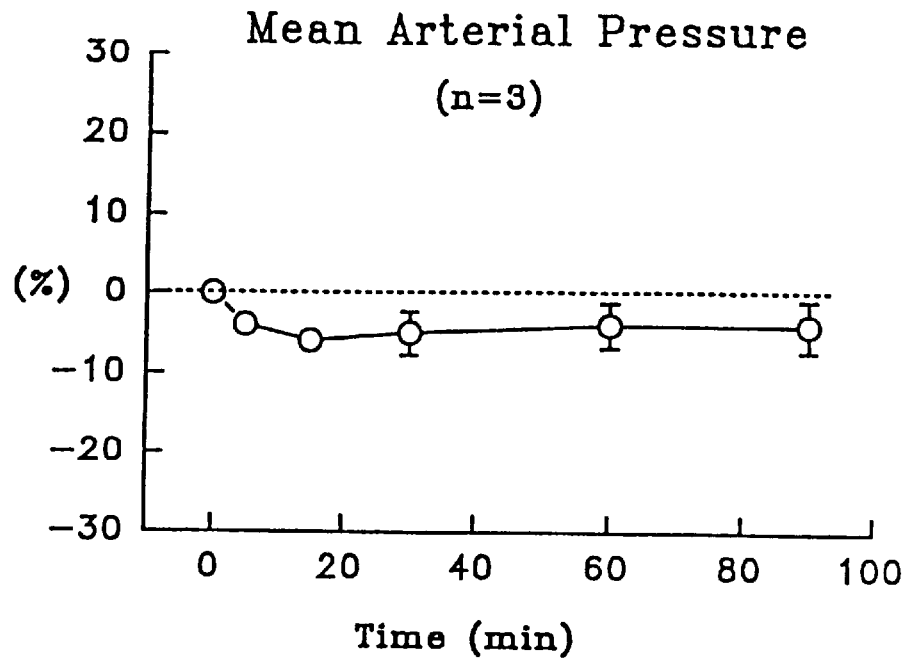
FIG. 14. Effects of Compound 3 (4 mg/kg, i.v.) on mean arterial pressure, total peripheral resistance, LV dP/dt, and Vcf in conscious pigs with heart failure. Values (mean±SE) are expressed as percent change from baseline.
Figure 14B:
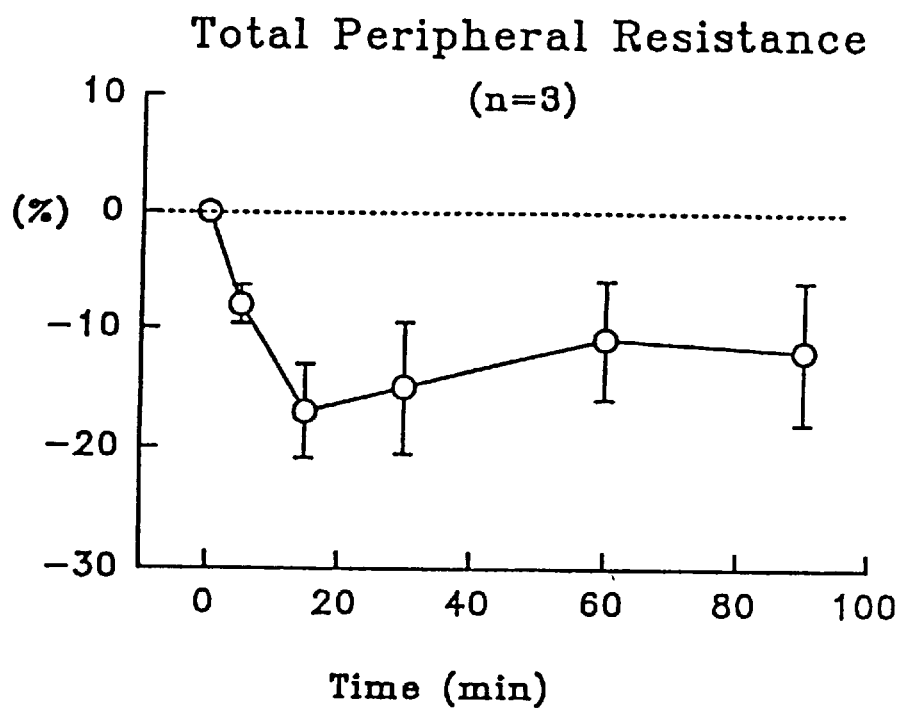
Figure 14C:
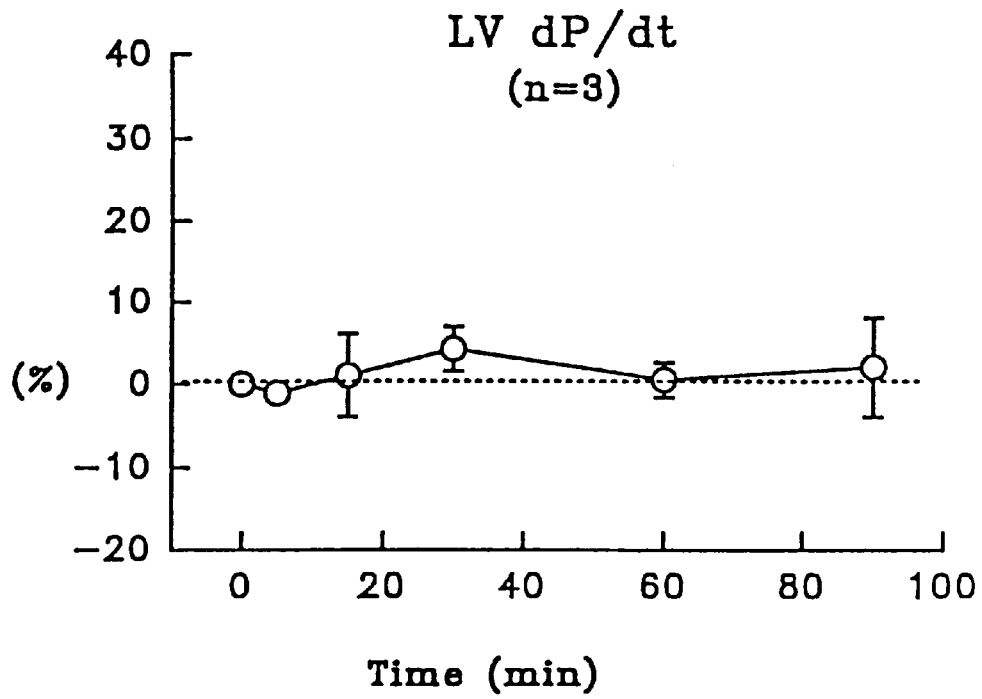
Figure 14D:
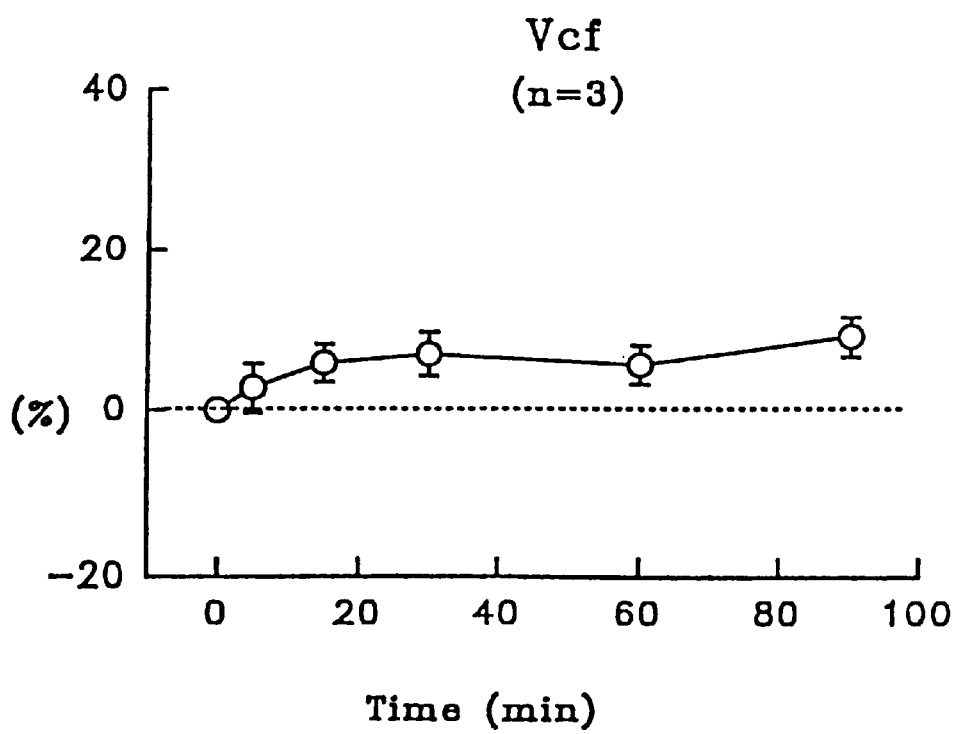
Figure 15A:
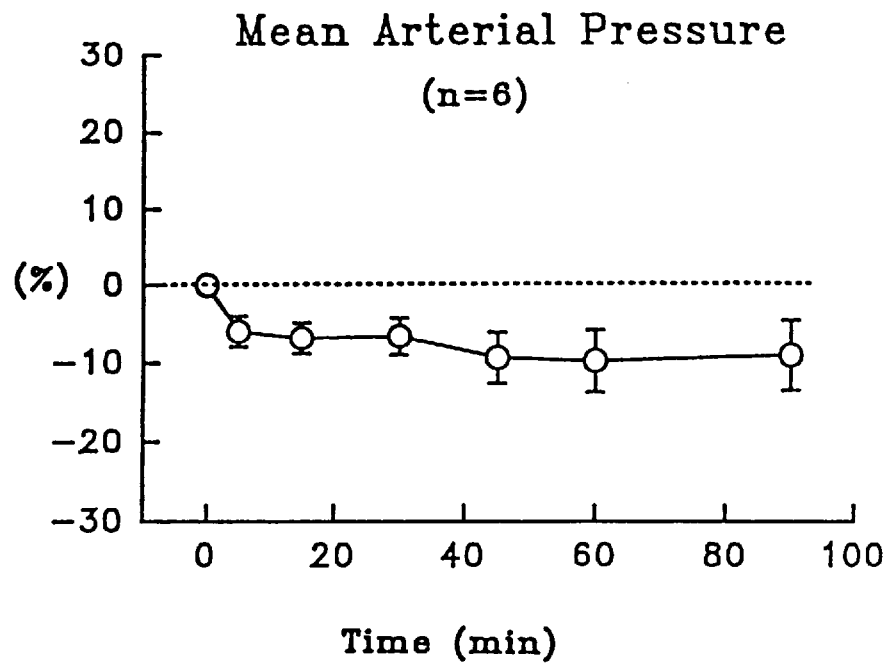
FIG. 15. Effects of combined Compound 2 and Compound 3 (each 1 mg/kg, i.v.) on mean arterial pressure, total peripheral resistance, LV dP/dt, and Vcf in conscious pigs with heart failure. The injection of Compound 3 was 30 min after injection of Compound 2. Values (mean±SE) are expressed as percent change from baseline.
Figure 15B:
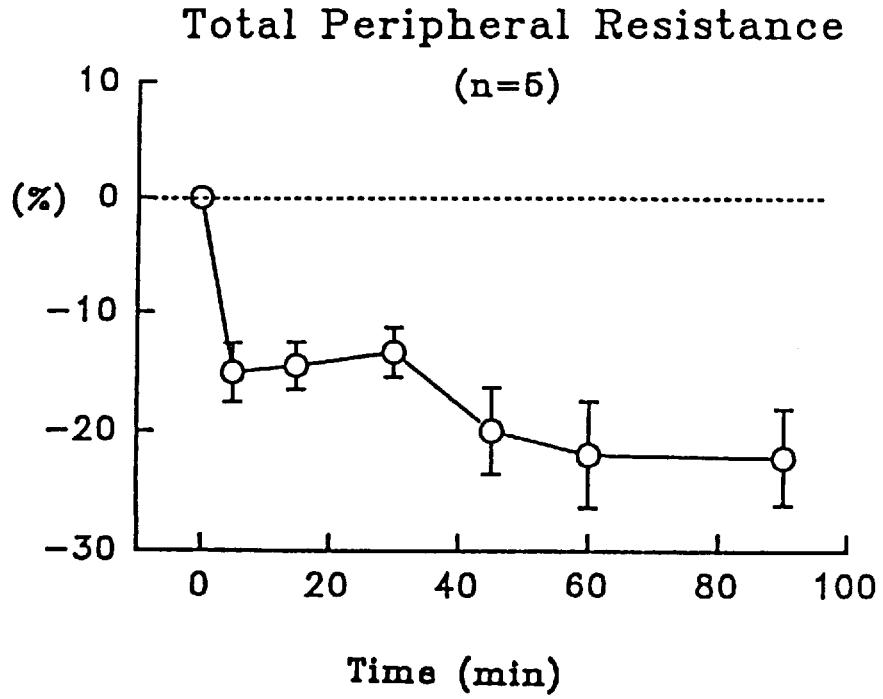
Figure 15C:
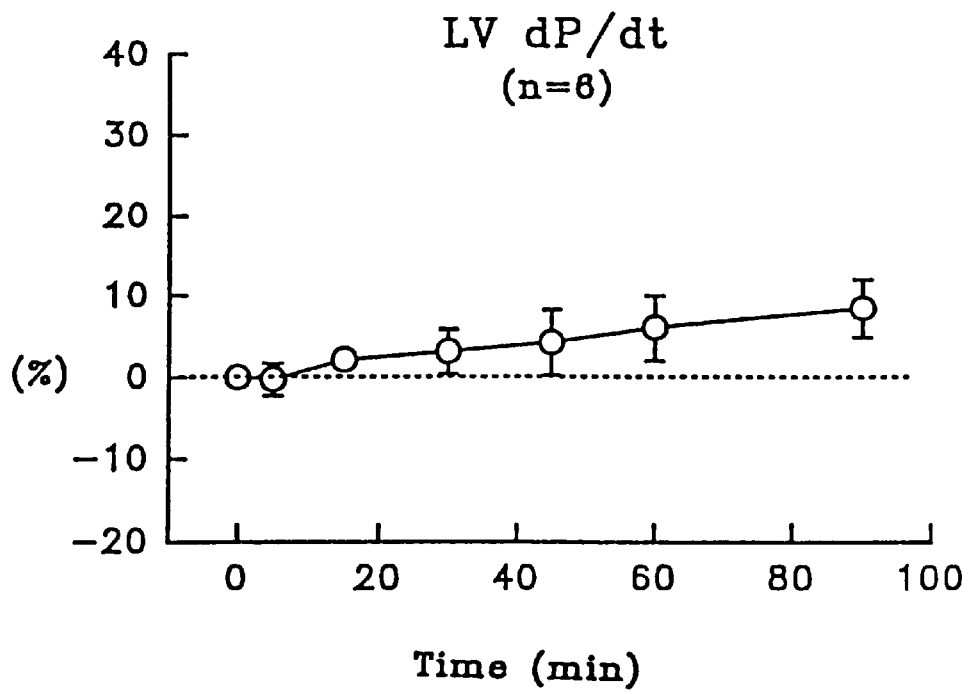
Figure 15D:
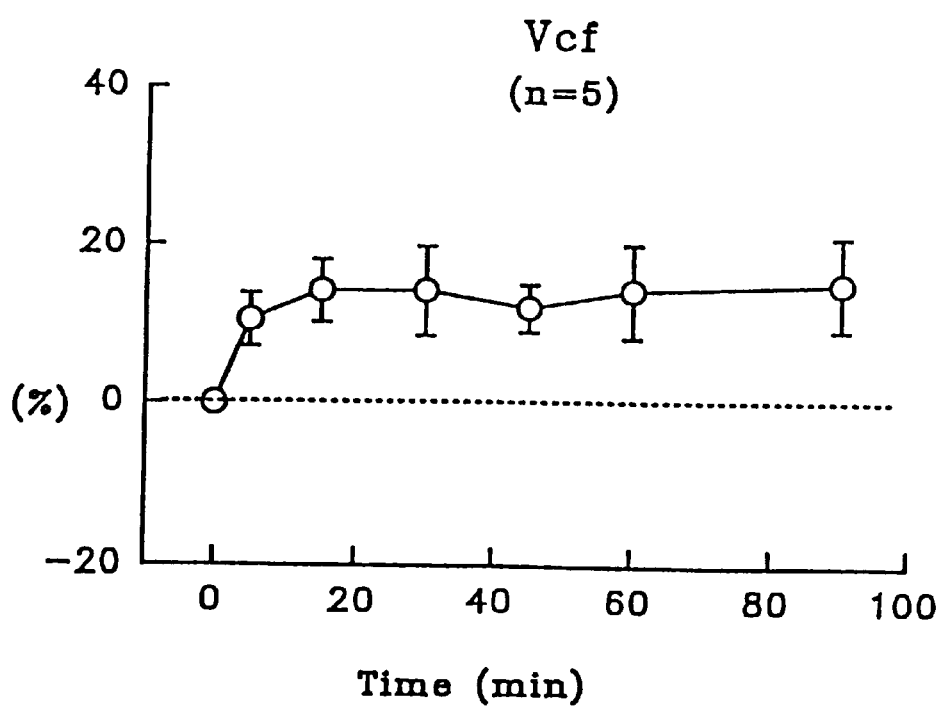
Figure 16A:
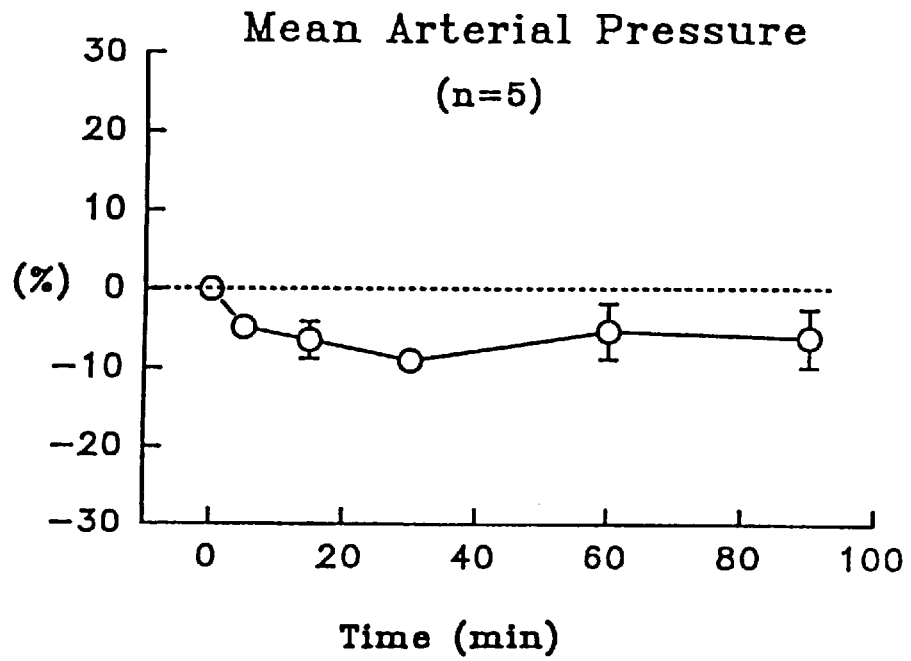
FIG. 16. Effects of combined Compound 2 and Compound 3 (each 1 mg/kg, i.v.) on mean arterial pressure, total peripheral resistance, LV dP/dt, and Vcf in conscious pigs with heart failure. Values (mean±SE) are expressed as percent change from baseline.
Figure 16B:
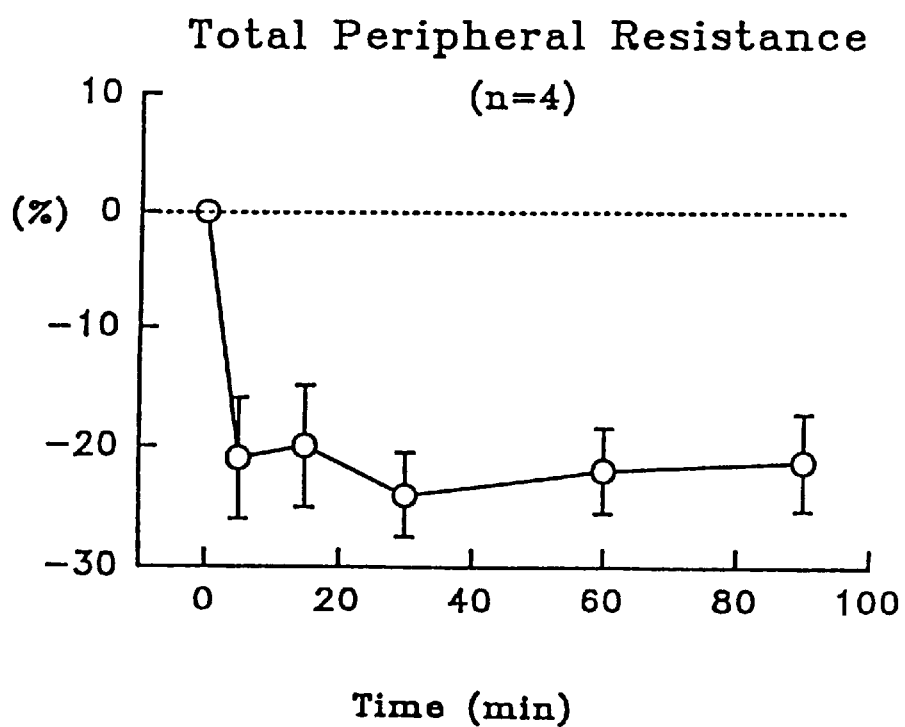
Figure 16C:
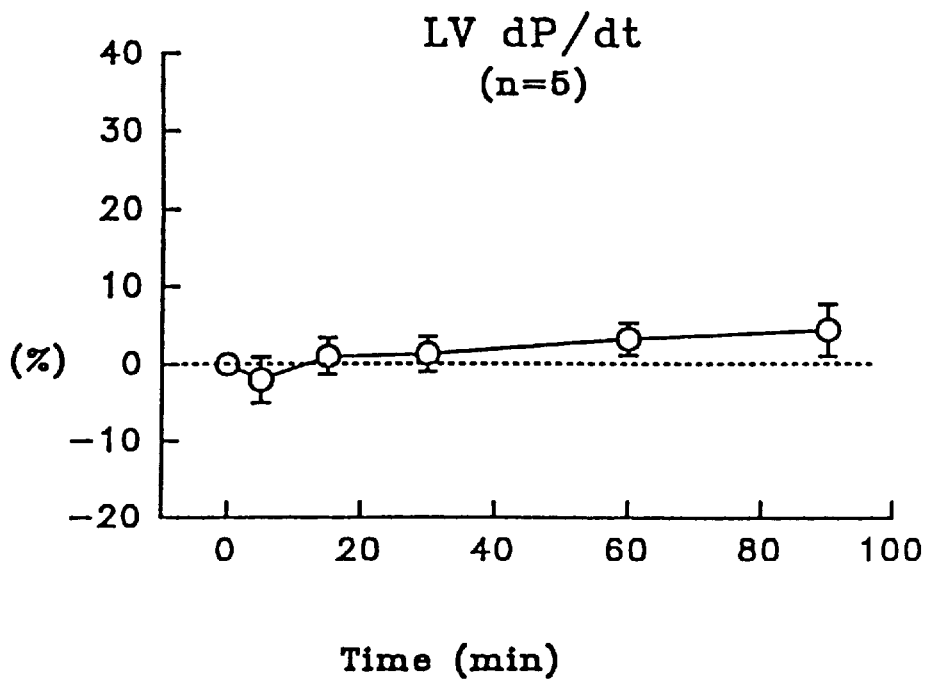
Figure 16D:
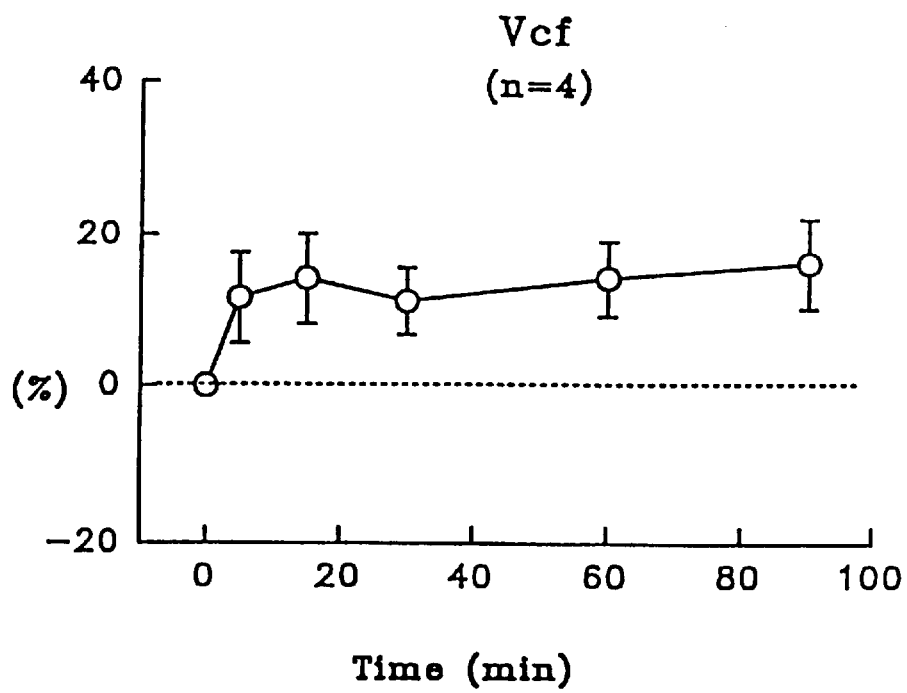

Tables 1 and 2 summarize the baseline LV function and systemic vascular dynamics before (i.e., post-surgical control) and after heart failure induced by serial myocardial infarctions followed by intermittent tachycardiac stress in conscious pigs. Heart failure resulting from at least 2 cycles of tachycardiac pacing in the presence of myocardial injury was manifested by significant increases in LV end-diastolic (+13.5±3.2 mm from 39.4±3.2 mm) and end-systolic diameters (+17.4±3.6 mm from 29.8±2.6 mm) and in mean left atrial pressure (+18±2 mmHg from 4±1 mmHg). LV dP/dt, LV fractional shortening, Vcf, and cardiac index significantly decreased by 43±8, 55±7, 51±6 and 36±5%, respectively. Also, total peripheral resistance increased significantly (+52±12%), while mean arterial pressure and heart rate were unchanged. In addition to these hemodynamic changes, which are shown in FIG. 9, heart failure, particularly at the advanced stages, was characterized by anorexia, peripheral and pulmonary edema, and reduced physical activity.

TABLE 1

Baseline Left Ventricular Function in Controls and Conscious Pigs with Heart Failure.

| | Control | Heart Failure |
|---|---|---|
| LV End-Diastolic Diameter (mm) | 39.4 ± 3.2 | 52.9 ± 2.5* |
| LV End-Systolic Diameter (mm) | 29.8 ± 2.6 | 47.2 ± 2.7* |
| LV Fractional Shortening (%) | 24.7 ± 1.8 | 10.9 ± 1.7* |
| Vcf (sec$^{-1}$) | 1.21 ± 0.10 | 0.58 ± 0.01* |
| LV dP/dt (mmHg/sec) | 2890 ± 124 | 1641 ± 208* |

*Significantly different from control, p<0.05.
Data are mean ± SE with n = 5 (n = 6 for LV dP/dt).

TABLE 2

Baseline Cardiac and Systemic Hemodynamics in Controls and Conscious Pigs with Heart Failure.

| | Control | Heart Failure |
|---|---|---|
| Mean Arterial Pressure (mmHg) | 92 ± 3 | 86 ± 3 |
| Mean Left Atrial Pressure (mmHg) | 4 ± 1 | 22 ± 2* |
| Cardiac Index (ml/min/kg) | 126 ± 9 | 80 ± 6* |
| Total Peripheral Resistance (mmHg/ml/min/kg) | 0.72 ± 0.06 | 1.08 ± 0.06* |
| Heart Rate (beat/min) | 128 ± 7 | 143 ± 11 |

*Significantly different from control, p<0.05.
Data are mean ± SE with n = 6 (n = 5 for cardiac index and total peripheral resistance).

Step C: Effects of Compound 2 and/or Compound 3 on Hemodynamics in Heart Failure FIGS. 10 through 16 show the time course of mean arterial pressure, total peripheral resistance, LV dP/dt and LV mean velocity of circumferential fiber shortening (Vcf) changes during each of the treatment protocols mentioned in the Methods Section. The vehicle (FIG. 10) did not induce any significant changes throughout 90 min of observation. Compound 2 (FIG. 11) and Compound 3 (FIG. 12), administered individually at doses of 1 mg/kg, each induced a minor decrease in mean arterial pressure, while total peripheral resistance was reduced by approximately 15% from baseline levels. LV dP/dt was unchanged and Vcf was slightly increased by administration of these compounds. Compound 2 (FIG. 13) and Compound 3 (FIG. 14), administered individually at high doses of 4 mg/kg, each caused similar changes in all indices compared to those observed at 1 mg/kg, indicating that the maximal effects of these agents had been achieved with the 1 mg/kg, i.v. doses. When Compound 3 (1 mg/kg) was injected either concomitantly or 30 min after Compound 2 (1 mg/kg) administered, the total peripheral resistance was reduced by more than 20% and Vcf was increased by approximately 10 to 15% from baseline levels (FIGS. 15 and 16).

Figure 17:
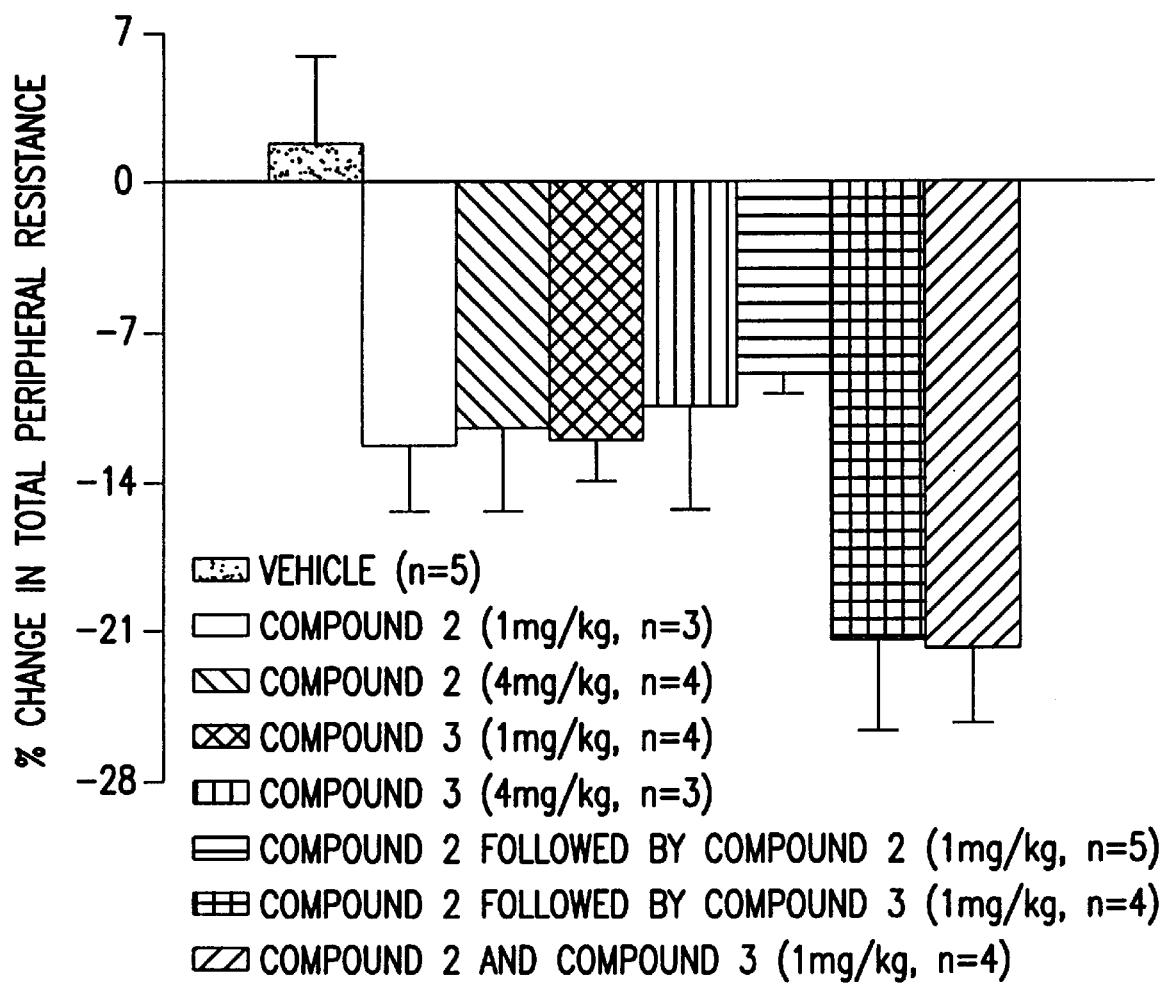
FIG. 17. Comparison of changes in total peripheral resistance at 60 min after injection of Compound 2 and/or Compound 3 in conscious pigs with heart failure. Values (mean±SE) are expressed as percent change from baseline.
Figure 18:
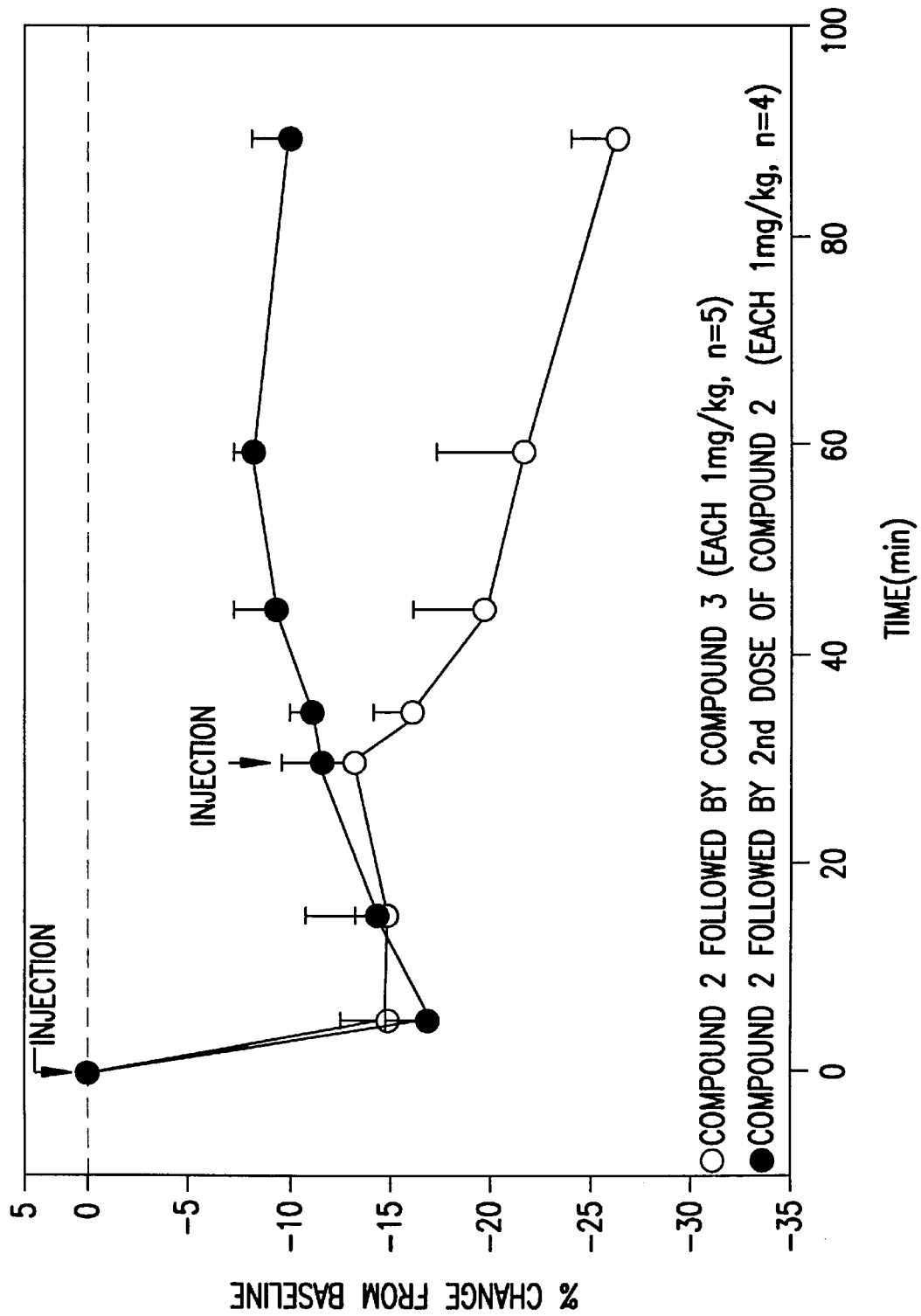
FIG. 18. Changes in total peripheral resistance following combined dose of Compound 2 and Compound 3 (each 1 mg/kg, i.v.) or two doses of Compound 2 (each 1 mg/kg, i.v.) in conscious pigs with heart failure. The dose of Compound 3 or the second dose of Compound 2 was administered 30 min after the initial dose of Compound 2. Values (mean±SE) are expressed as percent change from baseline.
Figure 19:
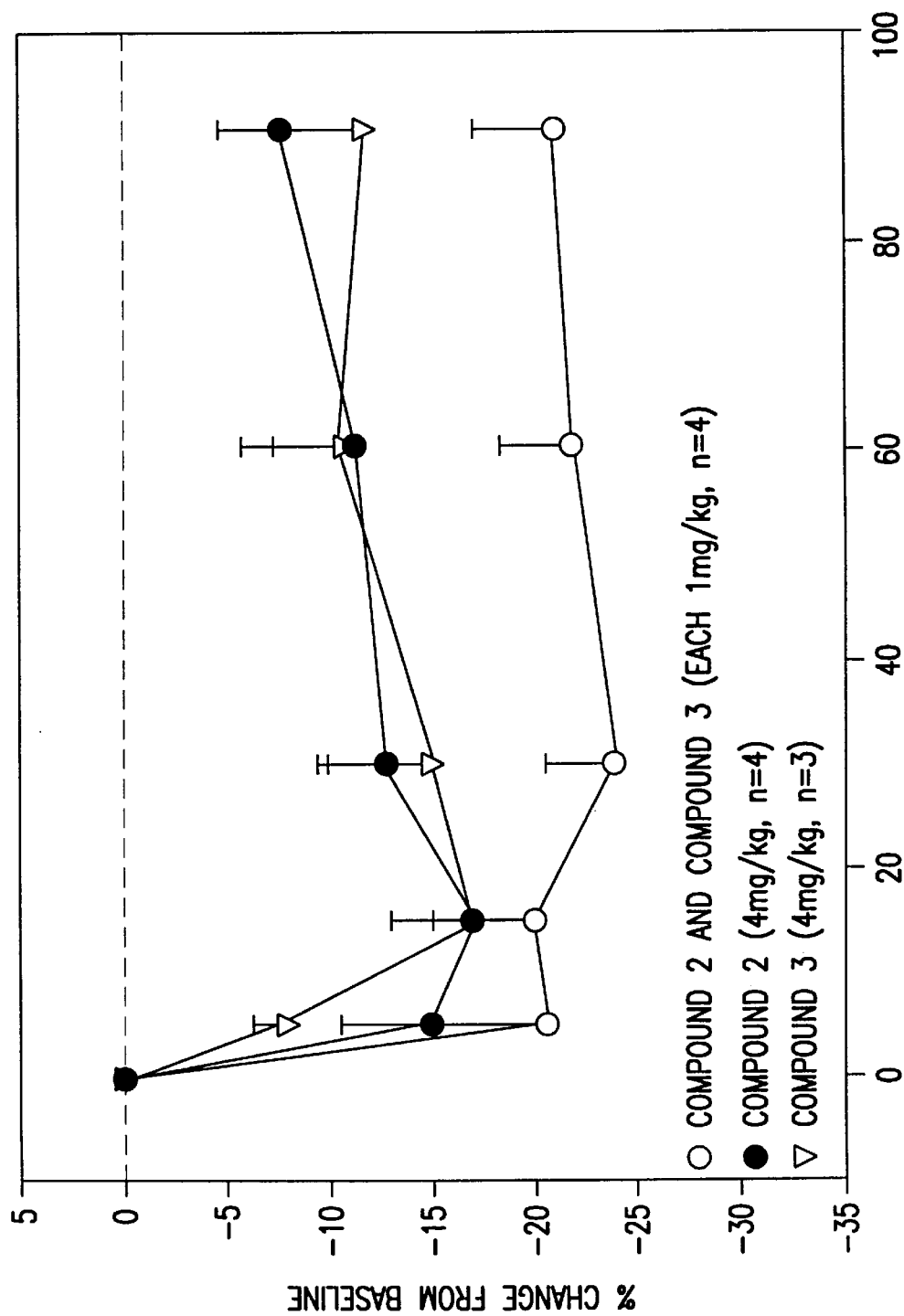
FIG. 19. Changes in total peripheral resistance following combined dose of Compound 2 and Compound 3 (each 1 mg/kg, i.v.) or single doses of Compound 2 (4 mg/kg, i.v.) or Compound 3 (4 mg/kg, i.v.) in conscious pigs with heart failure. Values (mean±SE) are expressed as percent change from baseline.

Step D: Combination Treatment Versus Mono-Treatment with Compound 2 and Compound 3 in Heart Failure FIG. 17 compares the effects of combination treatment with those of mono-treatment with Compound 2 and Compound 3 on total peripheral resistance 60 min after administration. The reduction in total peripheral resistance was greater following combination treatment than that following mono-treatment with either agent. FIG. 18 shows the time course of total peripheral resistance changes after separate administrations either of Compound 2 (1 mg/kg) and Compound 3 (1 mg/kg) or of two doses of Compound 2 (each 1 mg/kg). Clearly, Compound 3 enhanced the reduction in total peripheral resistance in the presence of Compound 2, whereas a second dose of Compound 2 did not have the same effect. Also, Compound 2 and Compound 3 administered together (each 1 mg/kg) decreased total peripheral resistance more than even a higher, single dose of Compound 2 (4 mg/kg) or Compound 3 (4 mg/kg) alone (FIG. 19).

Figure 20:
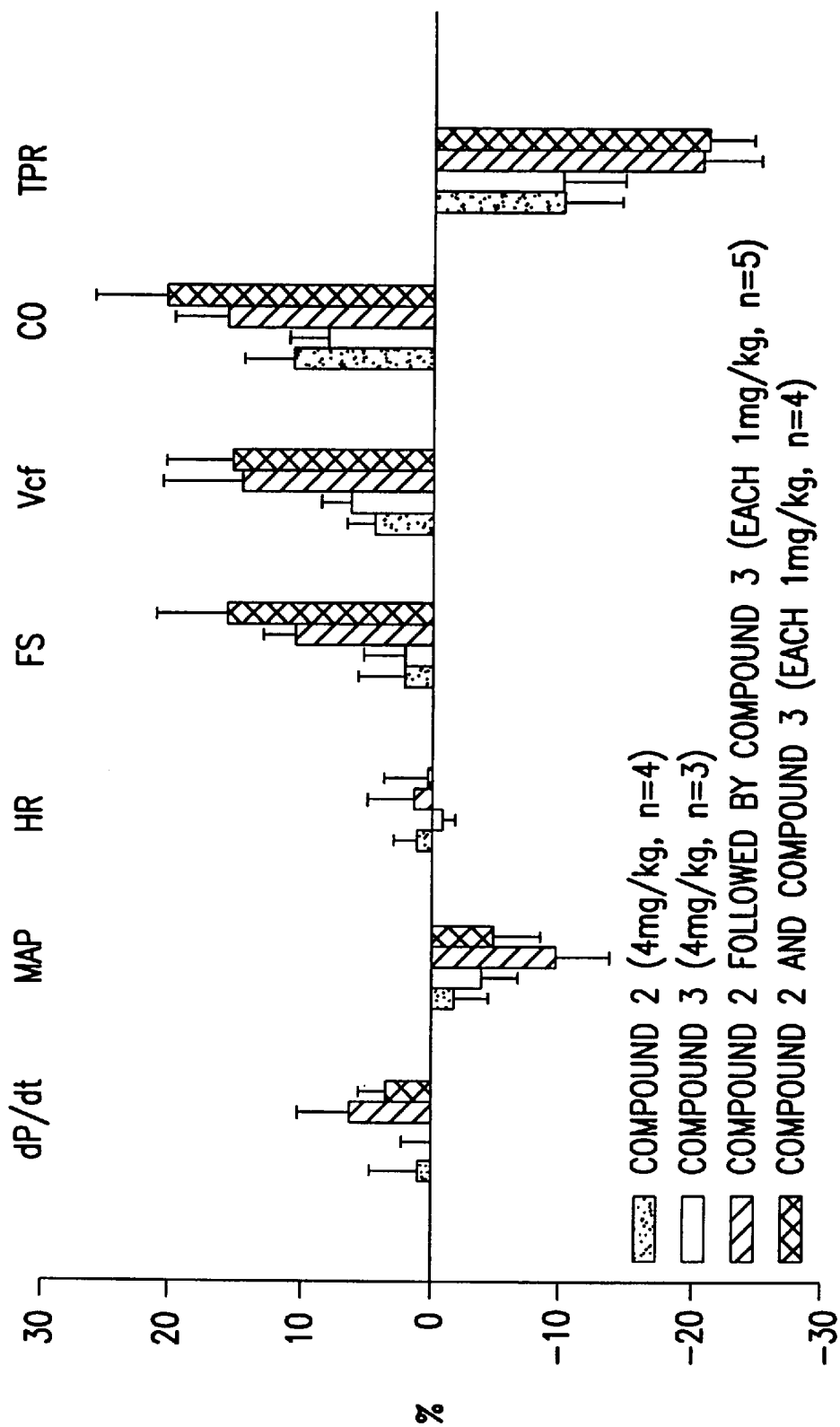
FIG. 20. Effects of combined treatment and mono-treatment with Compound 2 and Compound 3 on LV dP/dt, mean arterial pressure (MAP), heart rate (HR), fractional shortening (FS), velocity of circumferential fiber shortening (Vcf), cardiac output (CO) and total peripheral resistance (TPR) 60 min after injection in conscious pigs with heart failure. Values (mean±SE) are expressed as percent change from baseline.
Figure 21A:
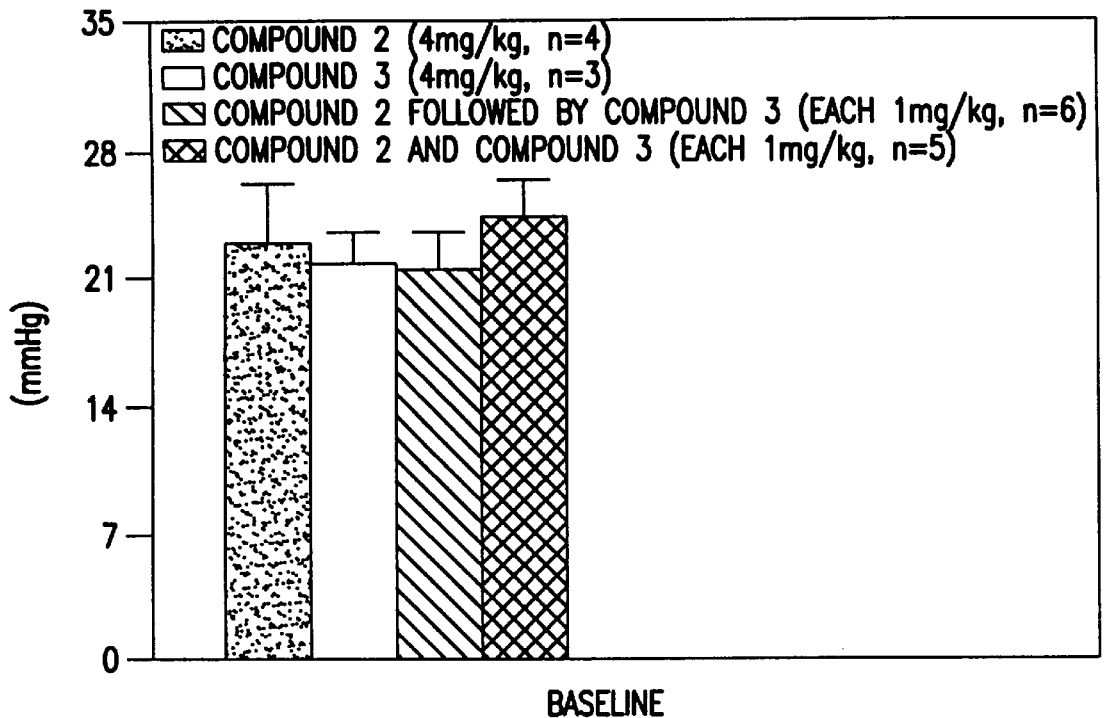
FIG. 21. Effects of combined treatment and mono-treatment with Compound 2 and Compound 3 on mean left atrial pressure at baseline and 60 min after injection in conscious pigs with heart failure. Values (mean±SE) are expressed as change from baseline.
Figure 21B:
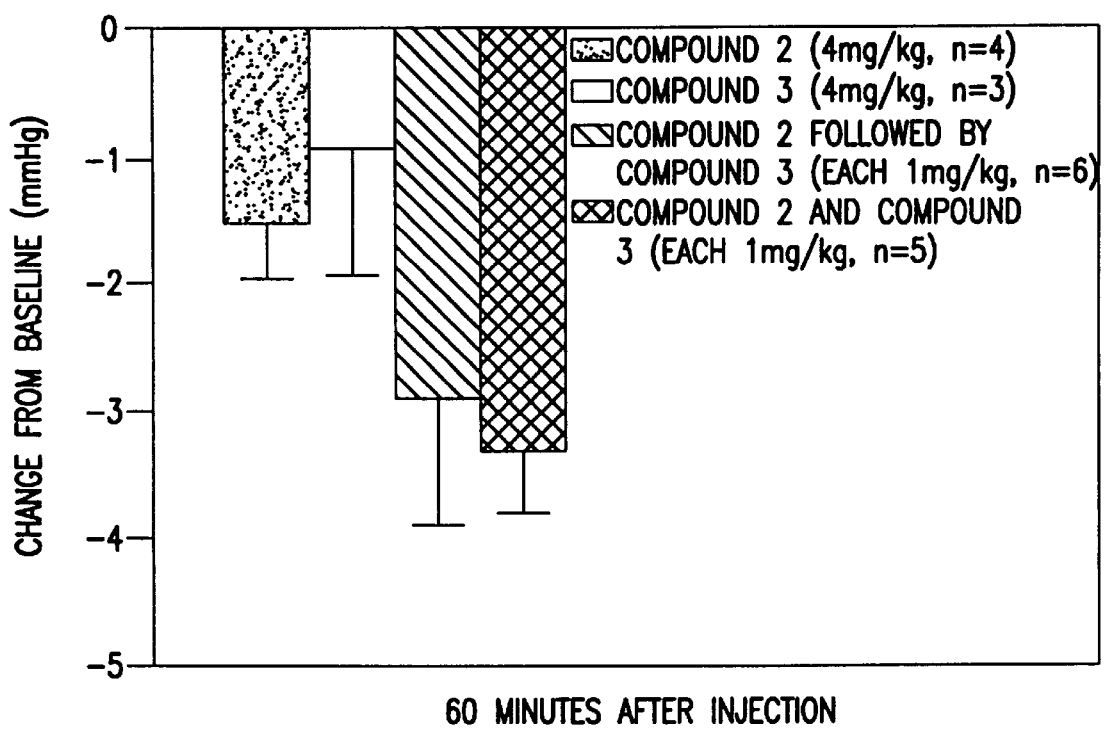

FIG. 20 compares the effects of combination treatment versus mono-treatment with Compound 2 and Compound 3 on LV dP/dt, mean arterial pressure, heart rate, fractional shortening, Vcf, cardiac output and total peripheral resistance 60 min after injection. The increases in fractional shortening, Vcf, and cardiac output were greater in response to the combination treatment than in response to the mono-treatment with either agent. The effects on mean left atrial pressure are shown in FIG. 21. The baseline left atrial pressure was similar in all groups, whereas left atrial pressure was reduced more in the combination treatment groups than in the mono-treatment groups.

These preliminary data suggest that treatment with the ACE inhibitor, Compound 2 (enalaprilat), in combination with a selective AII antagonist, Compound 3 (Compound 3) reduced vascular resistance and left atrial pressure and increased cardiac output during heart failure more effectively than either compound alone. None of the treatments affected myocardial contractility as evidenced by the lack of significant changes in LV dP/dt. The increases in ejection phase indices therefore could be due to the decrease in afterload.

What is claimed is:

1. A method for simulating heart failure in a conscious, animal instrumented with aortic catheter, aortic flow probe, right atrial catheter, a cardiac pacemaker with right ventricular and left atrial pacing leads, left ventricular pressure gauge, left atrial catheter, two hydraulic occluders (distal and proximal), and left ventricular diameter crystal comprising the steps of:

(a) producing myocardial ischemia in the instrumented animal; and (b) introducing rapid cardiac pacing in the instrumented animal, until the hemodynamic measurements are indicative of heart failure, wherein hemodynamic measurements include: left atrial pressures; arterial pressure; aortic blood flow; total peripheral resistance; left ventricular end-diastolic dimension; left ventricular end systolic dimension; fractional shortening, mean velocity of circumferential fiber shortening and regional blood flows.

2. The method for simulating heart failure in a conscious, instrumented animal as recited in claim 1, wherein production of myocardial ischemia comprises the steps of:

(a) inflating the distally implanted hydraulic occluder of the instrumented animal to occlude the distal left circumflex coronary artery;

(b) waiting about 6 hours to 30 days after the distal left circumflex coronary artery occlusion; and (c) inflating the proximally implanted hydraulic occluder of the instrumented animal to occlude the proximal left circumflex coronary artery.

3. The method for simulating heart failure in a conscious, instrumented animal as recited in claim 2, wherein the rapid cardiac pacing comprises the steps of:

(a) using the cardiac pacemaker of the instrumented animal to introduce rapid cardiac pacing at a rate of about 190–210 beats/minute for about 1 to 7 days;

(b) waiting for about 0 to 72 hours after the first pacing; and (c) repeating steps (a) and (b) at least until the hemodynamic measurements are indicative of heart failure, wherein hemodynamic measurements include: left atrial pressures; arterial pressure; aortic blood flow; total peripheral resistance; left ventricular end-diastolic dimension; left ventricular end systolic dimension; fractional shortening, mean velocity of circumferential fiber shortening and regional blood flows.

4. The method for simulating heart failure in a conscious, instrumented animal as recited in claim 3, wherein the rapid cardiac pacing is introduced in the left or right ventricle.

5. The method for simulating heart failure in a conscious, instrumented animal as recited in claim 3, wherein the rapid cardiac pacing is introduced in the left or right atrium.

6. The method for simulating heart failure in a conscious, instrumented animal as recited in claim 4, wherein the rapid cardiac pacing is introduced in the right ventricle.

7. The method for simulating heart failure in a conscious, instrumented animal as recited in claim 6, wherein the instrumented animal is selected from the group consisting of pig, monkey, baboon, rabbit, cat, dog, sheep, goat, horse and cow.

8. The method for simulating heart failure in a conscious, instrumented animal as recited in claim 7, wherein the instrumented animal is mobile.

9. The method for simulating heart failure in a conscious, instrumented animal as recited in claim 7, wherein the instrumented animal is immobile.

10. The method for simulating heart failure in a conscious, instrumented animal as recited in claim 9, wherein the instrumented animal is a pig.

11. A method for simulating heart failure in an immobilized, conscious pig, instrumented with aortic catheter, aortic flow probe, right atrial catheter, a cardiac pacemaker with right ventricular and left atrial pacing leads, left ventricular pressure gauge, left atrial catheter, two hydraulic occluders (distal and proximal), and left ventricular diameter crystal comprising the steps of:

(a) inflating the distally implanted hydraulic occluder of the instrumented pig to occlude the distal left circumflex coronary artery;

(b) waiting about 6 hours to 30 days after the distal left circumflex coronary artery occlusion; and (c) inflating the proximally implanted hydraulic occluder of the instrumented pig of the instrumented pig to occlude the proximal left circumflex coronary artery.

(d) waiting about 24 to about 48 hours after the proximal left circumflex coronary artery occlusion;

(e) using the cardiac pacemaker of the instrumented pig to introduce rapid cardiac pacing at a rate of about 190–210 beats/minute for about 1 to 7 days;

(f) waiting for about 0 to 72 hours after the first pacing; and (g) repeating steps (e) and (f) at least until the hemodynamic measurements are indicative of heart failure, wherein the hemodynamic measurements include: left atrial pressures; arterial pressure; aortic blood flow; total peripheral resistance; left ventricular end-diastolic dimension; left ventricular end systolic dimension; fractional shortening, mean velocity of circumferential fibre shortening and regional blood flows.

12. The method for simulating heart failure in an immobilized, conscious, instrumented pig as recited in claim 11, which comprises introducing the rapid cardiac pacing in the left or right ventricle.

13. The method for simulating heart failure in an immobilized, conscious, instrumented pig as recited in claim 12, which comprises introducing the rapid cardiac pacing in the right ventricle.

14. The method for simulating heart failure in an immobilized, conscious, instrumented pig as recited in claim 11, which comprises introducing the rapid cardiac pacing in the right or left atrium.

* * * * *